(12) United States Patent
el Kaliouby et al.

(10) Patent No.: US 11,587,357 B2
(45) Date of Patent: Feb. 21, 2023

(54) VEHICULAR COGNITIVE DATA COLLECTION WITH MULTIPLE DEVICES

(71) Applicant: Affectiva, Inc., Boston, MA (US)

(72) Inventors: Rana el Kaliouby, Milton, MA (US); Abdelrahman N. Mahmoud, Somerville, MA (US); Seyedmohammad Mavadati, Watertown, MA (US); Panu James Turcot, Pacifica, CA (US)

(73) Assignee: Affectiva, Inc., Boston, MA (US)

( * ) Notice: Subject to any disclaimer, the term of this patent is extended or adjusted under 35 U.S.C. 154(b) by 144 days.

(21) Appl. No.: 16/819,357

(22) Filed: Mar. 16, 2020

(65) Prior Publication Data

US 2020/0226355 A1 Jul. 16, 2020

Related U.S. Application Data

(63) Continuation-in-part of application No. 15/886,275, filed on Feb. 1, 2018, now Pat. No. 10,592,757, which
(Continued)

(51) Int. Cl.
*G06V 40/16* (2022.01)
*A61B 5/16* (2006.01)
(Continued)

(52) U.S. Cl.
CPC ............ *G06V 40/174* (2022.01); *A61B 5/165* (2013.01); *G06Q 30/0271* (2013.01);
(Continued)

(58) Field of Classification Search
CPC .......... G06K 9/00302; G06K 9/00315; G06K 9/00832; A61B 5/165; A61B 5/02055;
(Continued)

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP 08115367 7/1996
KR 10-2005-0021759 A 3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Wesley J Tucker
(74) *Attorney, Agent, or Firm* — Adams Intellex, PLC

(57) ABSTRACT

Vehicle cognitive data is collected using multiple devices. A user interacts with various pieces of technology to perform numerous tasks and activities. Reactions can be observed and cognitive states inferred from reactions to the tasks and activities. A first computing device within a vehicle obtains cognitive state data which is collected on an occupant of the vehicle from multiple sources, wherein the multiple sources include at least two sources of facial image data. At least one face in the facial image data is partially occluded. A second computing device generates analysis of the cognitive state data which is collected from the multiple sources. A third computing device renders an output which is based on the analysis of the cognitive state data. The partial occluding includes a time basis of occluding. The partial occluding includes an image basis of occluding. The cognitive state data from multiple sources is tagged.

26 Claims, 17 Drawing Sheets

Related U.S. Application Data is a continuation-in-part of application No. 15/875,644, filed on Jan. 19, 2018, now Pat. No. 10,627,817, and a continuation-in-part of application No. 15/273,765, filed on Sep. 23, 2016, now abandoned, and a continuation-in-part of application No. 14/796,419, filed on Jul. 10, 2015, now abandoned, and a continuation-in-part of application No. 14/460,915, filed on Aug. 15, 2014, now abandoned, and a continuation-in-part of application No. 13/153,745, filed on Jun. 6, 2011, now abandoned, said application No. 15/886,275 is a continuation of application No. 14/064,136, filed on Oct. 26, 2013, now Pat. No. 9,204,836, which is a continuation of application No. 14/144,413, filed on Dec. 30, 2013, now Pat. No. 9,934,425, and a continuation-in-part of application No. 13/153,745, filed on Jun. 6, 2011, now abandoned.

(60) Provisional application No. 62/955,493, filed on Dec. 31, 2019, provisional application No. 62/954,819, filed on Dec. 30, 2019, provisional application No. 62/954,833, filed on Dec. 30, 2019, provisional application No. 62/925,990, filed on Oct. 25, 2019, provisional application No. 62/926,009, filed on Oct. 25, 2019, provisional application No. 62/893,298, filed on Aug. 29, 2019, provisional application No. 62/827,088, filed on Mar. 31, 2019, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010, provisional application No. 61/844,478, filed on Jul. 10, 2013, provisional application No. 61/789,038, filed on Mar. 15, 2013, provisional application No. 61/790,461, filed on Mar. 15, 2013, provisional application No. 61/793,761, filed on Mar. 15, 2013, provisional application No. 61/798,731, filed on Mar. 15, 2013, provisional application No. 61/747,651, filed on Dec. 31, 2012, provisional application No. 61/747,810, filed on Dec. 31, 2012, provisional application No. 61/719,383, filed on Oct. 27, 2012.

(51) Int. Cl.
| | |
|---|---|
| *G06Q 30/02* | (2012.01) |
| *G16H 20/40* | (2018.01) |
| *G16H 80/00* | (2018.01) |
| *G06Q 50/00* | (2012.01) |
| *A61B 5/024* | (2006.01) |
| *A61B 5/0533* | (2021.01) |
| *A61B 5/08* | (2006.01) |
| *A61B 5/11* | (2006.01) |
| *A61B 5/0205* | (2006.01) |
| *G06Q 30/0251* | (2023.01) |

(52) U.S. Cl.
CPC ............ *G16H 20/40* (2018.01); *G16H 80/00* (2018.01); *A61B 5/02055* (2013.01); *A61B 5/02405* (2013.01); *A61B 5/0533* (2013.01); *A61B 5/08* (2013.01); *A61B 5/11* (2013.01); *G06Q 50/01* (2013.01)

(58) Field of Classification Search
CPC ..... A61B 5/02405; A61B 5/0533; A61B 5/08; A61B 5/11; A61B 5/18; A61B 5/6893; G06Q 30/0271; G06Q 50/01; G16H 20/40; G16H 80/00; G16H 30/20; G16H 30/40; G16H 40/63; G16H 40/67; G16H 50/20
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |

(56) References Cited

U.S. PATENT DOCUMENTS

| | | |
|---|---|---|
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,724,920 B1 | 4/2004 | Berenz et al. |
| 6,792,458 B1 | 9/2004 | Muret et al. |
| 6,847,376 B2 | 1/2005 | Engeldrum et al. |
| 6,927,694 B1 | 8/2005 | Smith et al. |
| 7,003,135 B2 | 2/2006 | Hsieh et al. |
| 7,013,478 B1 | 3/2006 | Hendricks et al. |
| 7,027,621 B1 * | 4/2006 | Prokoski ............ G06K 9/00248 |
| | | 180/272 |
| 7,110,570 B1 | 9/2006 | Berenz et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,300,891 B2 | 10/2012 | Chen et al. |
| 8,369,608 B2 | 2/2013 | Gunaratne |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 8,947,217 B2 | 2/2015 | Moussa et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0011399 A1 | 1/2006 | Brockway et al. |
| 2006/0019224 A1 | 1/2006 | Behar et al. |
| 2006/0143647 A1 | 6/2006 | Bill |
| 2006/0149428 A1 | 7/2006 | Kim et al. |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0167757 A1 | 7/2008 | Kanevsky et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0134302 A1 | 6/2010 | Ahn et al. |

(56) References Cited

U.S. PATENT DOCUMENTS

| | | |
|---|---|---|
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0109452 A1 | 5/2012 | Autran et al. |
| 2012/0150430 A1 | 6/2012 | French et al. |
| 2012/0271484 A1 | 10/2012 | Feit et al. |
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2014/0171752 A1 | 6/2014 | Park et al. |
| 2014/0172910 A1 | 6/2014 | Jung et al. |
| 2014/0218187 A1 | 8/2014 | Chun et al. |
| 2015/0258995 A1 | 9/2015 | Essers et al. |
| 2016/0104486 A1* | 4/2016 | Penilla .................. G10L 15/005 704/232 |
| 2017/0003784 A1 | 1/2017 | Garg et al. |
| 2017/0297587 A1 | 10/2017 | Mimura et al. |
| 2018/0050696 A1 | 2/2018 | Misu et al. |
| 2018/0251122 A1 | 9/2018 | Golston et al. |
| 2019/0049965 A1 | 2/2019 | Tanriover |
| 2019/0135325 A1 | 5/2019 | Lisseman et al. |
| 2019/0176837 A1 | 6/2019 | Williams et al. |
| 2020/0103980 A1 | 4/2020 | Katz et al. |
| 2020/0171977 A1 | 6/2020 | Jales Costa et al. |
| 2020/0223362 A1 | 7/2020 | Witte |
| 2020/0285871 A1 | 9/2020 | Tokizaki et al. |
| 2020/0130528 A1 | 10/2020 | Upmanue et al. |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/039282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

Fasel, B. (Aug. 2002). Robust face analysis using convolutional neural networks. In Object recognition supported by user interaction for service robots (vol. 2, pp. 40-43). IEEE.

Matsugu, M., Mori, K., Mitari, Y., & Kaneda, Y. (2003). Subject independent facial expression recognition with robust face detection using a convolutional neural network. Neural Networks, 16(5-6), 555-559.

* cited by examiner

VEHICULAR COGNITIVE DATA COLLECTION WITH MULTIPLE DEVICES

RELATED APPLICATIONS

This application claims the benefit of U.S. provisional patent applications "Synthetic Data Augmentation for Neural Network Training" Ser. No. 62/954,819, filed Dec. 30, 2019, "Synthetic Data for Neural Network Training Using Vectors" Ser. No. 62/954,833, filed Dec. 30, 2019, "Autonomous Vehicle Control Using Longitudinal Profile Generation" Ser. No. 62/955,493, filed Dec. 31, 2019, "Image Analysis for Human Perception Artificial Intelligence" Ser. No. 62/827,088, filed Mar. 31, 2019, "Vehicle Interior Object Management" Ser. No. 62/893,298, filed Aug. 29, 2019, "Deep Learning In Situ Retraining" Ser. No. 62/925,990, filed Oct. 25, 2019, and "Data Versioning for Neural Network Training" Ser. No. 62/926,009, filed Oct. 25, 2019.

This application is also a continuation-in-part of U.S. patent application "Vehicular Cognitive Data Collection Using Multiple Devices" Ser. No. 15/886,275, filed Feb. 1, 2018, which claims the benefit of U.S. provisional patent applications "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation Using Translation Vectors" Ser. No. 62/593,440, filed Dec. 1, 2017, and "Directed Control Transfer for Autonomous Vehicles" Ser. No. 62/611,780, filed Dec. 29, 2017.

The U.S. patent application "Vehicular Cognitive Data Collection Using Multiple Devices" Ser. No. 15/886,275, filed Feb. 1, 2018 is also a continuation-in-part of U.S. patent application "Collection of Affect Data from Multiple Mobile Devices" Ser. No. 14/144,413, filed Dec. 30, 2013, which claims the benefit of U.S. provisional patent applications "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013.

The U.S. patent application "Collection of Affect Data from Multiple Mobile Devices" Ser. No. 14/144,413, filed Dec. 30, 2013 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Collection of Affect Data from Multiple Mobile Devices" Ser. No. 14/144,413, filed Dec. 30, 2013 is also a continuation-in-part of U.S. patent application "Sporadic Collection of Mobile Affect Data" Ser. No. 14/064,136, filed Oct. 26, 2012, which claims the benefit of U.S. provisional patent applications "Sporadic Collection of Affect Data" Ser. No. 61/719,383, filed Oct. 27, 2012, "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013.

The U.S. patent application "Collection of Affect Data from Multiple Mobile Devices" Ser. No. 14/144,413, filed Dec. 30, 2013 is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Vehicular Cognitive Data Collection Using Multiple Devices" Ser. No. 15/886,275, filed Feb. 1, 2018 is also a continuation-in-part of U.S. patent application "Vehicle Manipulation using Occupant Image Analysis" Ser. No. 15/875,644, filed Jan. 19, 2018, which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation Using Translation Vectors" Ser. No. 62/593,440, filed Dec. 1, 2017, and "Directed Control Transfer for Autonomous Vehicles" Ser. No. 62/611,780, filed Dec. 29, 2017.

The U.S. patent application "Vehicle Manipulation using Occupant Image Analysis" Ser. No. 15/875,644, filed Jan. 19, 2018 is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The U.S. patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF ART

This application relates generally to cognitive state analysis and more particularly to vehicular cognitive data collection with multiple devices.

BACKGROUND

People endeavor to travel, whether they love to do so or not. Common travel purposes include daily obligations, business travel, and adventure, among many others. People are moved from one location to another for financial reasons such as commuting to and from work or school, for personal reasons such as pleasure, relaxation, or discovery, or for exercise. Other causes of travel arise from undesirable or desperate situations which result from terrible events such as war, famine, or natural disaster. When people have the option to do so, they choose a mode of transportation based on the purpose of the travel and the modes of transportation available. Further travel considerations proceed from the convenience of a mode of transportation, availability of the types of transportation, or ultimately, cost. Personal and commercial modes of transportation include ground transportation, water transportation, and air transportation. Ground transportation can be accomplished on foot, by animal, or by vehicle such as a bicycle, a scooter, an automobile, a van, a bus, or a train. Water transportation can include using a personal vehicle such as a raft, canoe, or kayak, or a public vehicle such as a ferry or a ship, among others. Air transportation is most commonly accomplished using an airplane, but one could also travel in an airship, a balloon, or an ultralight. Travel most often involves a vehicle regardless of which mode of transportation is preferred by a person.

The amount of time that people spend in vehicles is significant. For many of those people, accrued travel time can reach hundreds of hours or more per year. The substantial portions of time that are committed to vehicular travel include waiting to be picked up by a vehicle, traveling in the vehicle, attempting to park the vehicle, waiting in security lines to get on a vehicle, waiting in line to collect baggage after traveling in the vehicle, among many other travel-related drudgeries. Typical vehicle-related travel events include the daily commute, taking the children to athletics practices, musical instrument lessons, or coding club, taking the pets to the veterinary clinic, shopping for food or household items, traveling, or any of the other common activities that require transportation. Traveling in a vehicle is time consuming at best, and at worst, boring, frustrating, and irritating. Rush hour traffic, accidents, and poorly maintained roads, among many other situations, further complicate vehicular transportation. The difficulties of transportation are also compounded by operating an unfamiliar vehicle, traveling in an unfamiliar city, and particularly having to remember to drive on the opposite side of the road. Tragically, these transportation realities can cause catastrophic consequences. Irritated operators of vehicles can experience road rage, bullying, and other antisocial behaviors, while bored, sleepy, impaired, distracted, or inattentive drivers, can cause vehicular accidents and resulting injury to themselves, occupants of other vehicles, pedestrians, bicyclists, and animals, and damage to 1property.

SUMMARY

Cognitive state analysis is based on vehicular cognitive data collection using multiple devices. The multiple devices can include cameras, microphones, portable electronic devices, sensors, and so on. The vehicle can be a standard vehicle, and autonomous vehicle, or a semi-autonomous vehicle. A first computing device within a vehicle is used to obtain cognitive state data which is collected on an occupant of the vehicle from multiple sources. The occupant of the vehicle can be the operator of the vehicle or a passenger within the vehicle. The multiple sources include at least two sources of facial image data. The at least two sources of facial image data can include one or more of an inside vehicle camera, an outside vehicle camera, a webcam, a phone camera, a tablet camera, a wearable camera, a room camera, a mobile device, a cell phone, a tablet computer, or a laptop computer. A face in the facial image data can be occluded or partially occluded. The multiple sources can include audio data such as voice data and physiological data such as heart rate, etc. The audio data can be collected using a microphone. The physiological data can be collected with other sensors. A second computing device is used to generate analysis of the cognitive state data which is collected from the multiple sources. The analysis can include aggregating the cognitive state data from the multiple sources. The analysis of the cognitive state data can be obtained from a web service. A third computing device renders an output based on the analysis of the cognitive state data. The rendering can include providing an emotigraphic profile. The rendering is used to provide vehicle performance data to one or more occupants of the vehicle. The rendering can be a visual rendering or an auditory rendering.

A computer-implemented method for cognitive state analysis is disclosed comprising: obtaining, on a first computing device within a vehicle, cognitive state data which is collected on an occupant of the vehicle from multiple sources, wherein the multiple sources include at least two sources of facial image data, and wherein at least one face is partially occluded; generating, using a second computing device, analysis of the cognitive state data which is collected from the multiple sources; and rendering, on a third computing device, an output based on the analysis of the cognitive state data. In embodiments, the partial occluding comprises a time basis of occluding. In embodiments, the partial occluding comprises an image basis of occluding. In embodiments, the cognitive state data from multiple sources is tagged. In embodiments, the facial image data is collected intermittently while the occupant's face is partially occluded.

In embodiments, a computer program product is embodied in a non-transitory computer readable medium for cognitive state analysis, the computer program product comprising code which causes one or more processors to perform operations of: obtaining cognitive state data which is collected on an occupant of a vehicle from multiple sources, wherein the multiple sources include at least two sources of facial image data; generating analysis of the cognitive state data which is collected from the multiple sources; and rendering an output based on the analysis of the cognitive state data.

Further embodiments comprise collecting audio data and augmenting the cognitive state data with the audio data. The audio data includes voice data. The voice data can be evaluated for timbre, prosody, vocal register, vocal resonance, pitch, loudness, speech rate, or language content. In embodiments, the voice data includes non-speech vocalizations. The non-speech vocalizations can include grunts, yelps, squeals, snoring, sighs, laughter, filled pauses, unfilled pauses, or yawns. The cognitive state data from multiple sources is tagged. The cognitive state data can be tagged with an identity value for the occupant of a vehicle. The cognitive state data can be tagged with information on a context in which the cognitive state data was collected. The rendering can be used to provide vehicle performance data to one or more occupants of the vehicle. The rendering can be used to provide vehicle control to one or more occupants of the vehicle. The vehicle can be an autonomous vehicle or a semi-autonomous vehicle. Control can be transferred from an occupant to the autonomous or semi-autonomous vehicle, or from the autonomous or semi-autonomous vehicle to the occupant.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
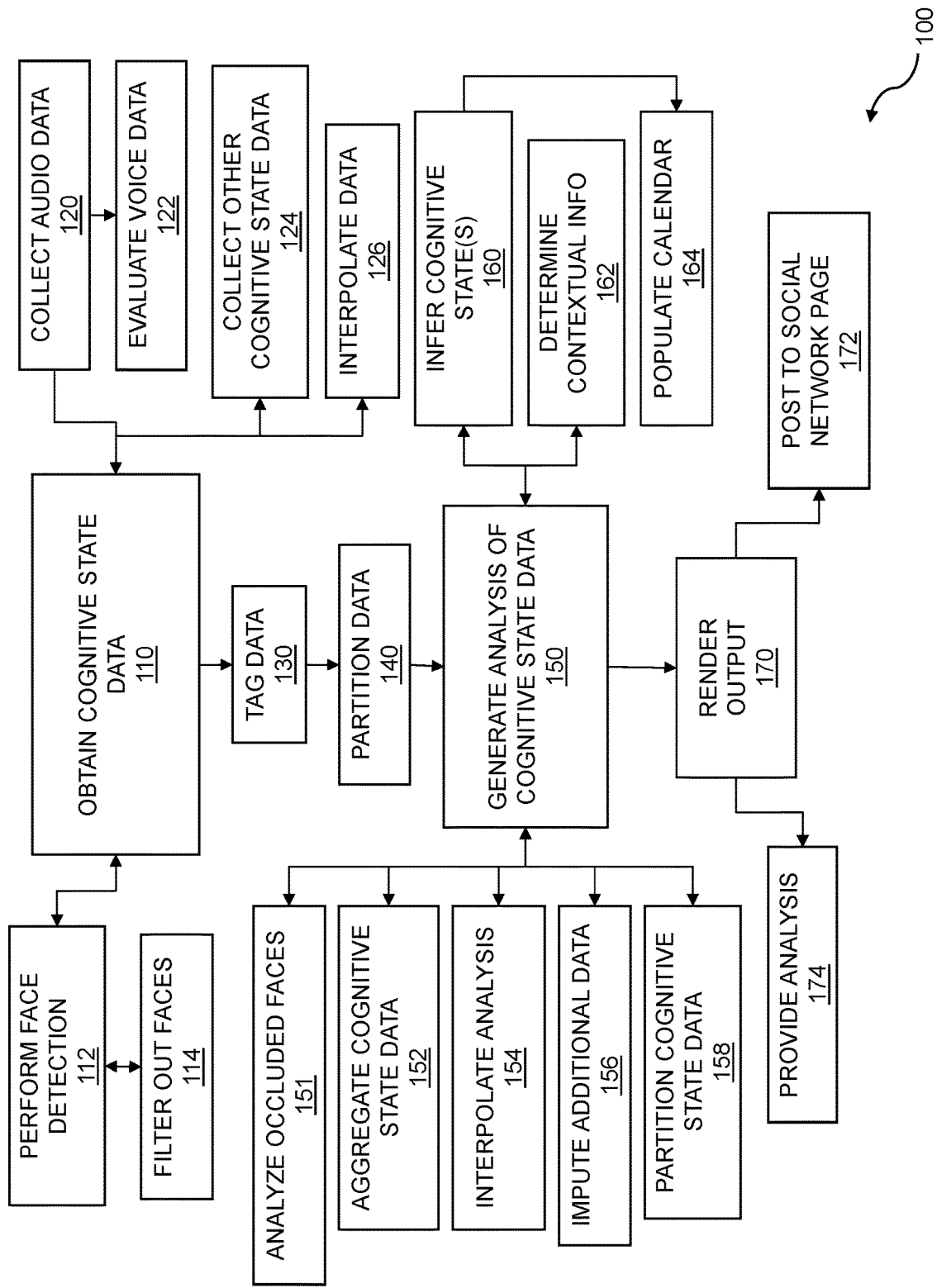
FIG. 1 is a flow diagram for cognitive state analysis.

Individuals can spend excessive amounts of time traveling in vehicles such as buses, trains, airplanes, automobiles, and so on. The hours, which can number in the hundreds or more per year, are spent commuting, running errands, traveling, etc. An individual traveling within or atop a vehicle presents a wide variety of cognitive states. The cognitive states can be inferred based on careful analysis of cognitive state data. The cognitive state data, which can be collected on the individual from various sources, can include image data, facial image data, audio data, voice data, speech data, non-speech data, physiological data, and so on. The facial image data can include one or more occluded or partially occluded faces. The occultation can cause a partially occluded face in the time domain, that is, the face can be occluded for some period of time and then become non-occluded for another period of time. The occultation can cause a partially occluded face in the image domain, that is, only a portion of the face is visible in the facial image data for a period of time or indefinitely. For example, only one eye of the face in the facial image data may be in the field of view. Various techniques are described to overcome the loss of image data due to a partially occluded face.

One or more cognitive states can be inferred, where the one or more cognitive states can be inferred based on analysis of the cognitive state data obtained from the multiple sources. The cognitive states can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. A rendering can be output based on the analysis of the cognitive state data. The rendering can be visual, auditory, or both. The rendering can be used to provide vehicle performance data to one or more occupants of the vehicle. The rendering can used to provide vehicle control to one or more occupants of the vehicle. The vehicle can be an autonomous vehicle or a semi-autonomous vehicle. The benefits of providing vehicle control to an occupant can include operational benefits, safety benefits, convenience benefits, and the like. The vehicle control can include a locking out operation; recommending a break for the occupant; recommending a different route; recommending how far to drive; responding to traffic; adjusting seats, mirrors, climate control, lighting, music, audio stimuli, interior temperature for the second vehicle; brake activation; steering control; etc.

In disclosed techniques, vehicular cognitive data collection uses multiple devices. Collected vehicular cognitive data, including multiple sources of cognitive state data from an occupant of the vehicle, can provide vehicle control to one or more occupants of the vehicle. The one or more occupants of the vehicle can be an operator of the vehicle, a passenger within the vehicle, and so on. The one or more occupants can have their faces occluded or partially occluded from an image collection device within or without the vehicle. The vehicle can be a standard vehicle, an autonomous vehicle, or a semi-autonomous vehicle. The providing vehicle control can include applying brakes, accelerating, steering, choosing travel routes, etc. A first computing device within a vehicle obtains cognitive state data which is collected on an occupant of the vehicle from multiple sources, wherein the multiple sources include at least two sources of facial image data. In embodiments, the multiple sources include at least one mobile device. In embodiments, the at least one mobile device includes a front-side camera. Further embodiments include collecting audio data and augmenting the cognitive state data with the audio data. Other sources of cognitive state data can include physiological data. A second computing device generates analysis of the cognitive state data which is collected from the multiple sources. A third computing device renders an output based on the analysis of the cognitive state data.

FIG. 1 is a flow diagram for cognitive state analysis. The flow 100 includes obtaining, on a first computing device within a vehicle, cognitive state data 110 which is collected on an occupant of the vehicle from multiple sources, wherein the multiple sources include at least two sources of facial image data. The at least two sources of facial image data can include one or more of an inside vehicle camera, an outside vehicle camera, a webcam, a phone camera, a tablet camera, a wearable camera, a room camera, a mobile device, a cell phone, a tablet computer, or a laptop computer, and the like. By using the facial image data obtained from multiple devices, more comprehensive cognitive state data can be collected. The facial image data can be collected using a camera, where the camera can include an in-vehicle camera, where the in-vehicle camera can include a video camera, a still camera, a thermal imager, a CCD device, a phone camera, a three-dimensional camera, a depth camera, a plenoptic camera, multiple webcams used to show different views of a person, or any other type of image capture apparatus that can allow captured data to be analyzed in an electronic system. The camera can be used to capture image data, where the image data includes the occupant of the vehicle. The image data can include other occupants of the vehicle. The facial image can be collected by a camera coupled to a mobile device such as a smartphone, a tablet, or the like. The camera can include a front-side camera coupled to the mobile device. In embodiments, the multiple sources include multiple cameras, each positioned with a different view of the occupant of the vehicle. The facial image data can be captured using two or more cameras which have different lines of sight with which to view the occupant.

In some embodiments, the facial image data is collected intermittently while the occupant of a vehicle is looking toward a camera. That is, facial image data can be collected while the occupant of the vehicle is looking toward the camera, and not collected when the occupant is looking away from the camera. This scenario can comprise partially occluded face on a time basis. The facial data can be collected intermittently from the individual because the user's face is not visible to any cameras. The intermittently collected data can be interpolated to determine cognitive state data that exists in the time between when an image is collected and a subsequent image is collected. This is different from the normal sequence of digital image collection where an image is typically processed at a rate of many frames per second. By interpolating, a more complete cognitive state analysis can be achieved, when the cognitive state data collected is intermittent. The interpolating generates interpolated data for time periods during which cognitive state data was not collected from one or more of the multiple sources, and hence additional, valuable cognitive state data can be used for cognitive sate analysis. The cognitive state data can include facial expressions. In embodiments, the cognitive state data can include one or more of smiles, laughter, smirks, grimaces, head position, up/down head motion, side-to-side head motion, tilting head motion, body leaning motion, or gaze direction. The cognitive state data interpolated, for example, could occur if an occupant wildly swings his face from side to side to indicate an emphatic "no" expression. The wild swinging can move the occupants face out of view and, absent interpolation, an accurate cognitive state analysis of the head motion could be missed. In some cases, the partially occluded face may be so near to absolute on either a time basis or an image basis that cognitive state data may only be collected and/or inferred by using audio data (described below) or by inferring cognitive state data based on image and/or audio data from other occupants of the vehicle. For example, a vehicle driver cannot be detected because the driver has intentionally blocked a camera directed to the driver's seat. Nonetheless, the conversation and images of other occupants can be analyzed to determine, for example, if they are comfortable with the driver's vehicle control, and an appropriate output rendering of the situation can be provided. Thus in embodiments, the partially occluded face comprises a fully occluded face, either on a time basis or an image basis.

The flow 100 further comprises performing face detection 112 to determine whether the occupant of a vehicle is looking toward the camera. The face detection can be based on extracting facial features from one or more faces that can be present in the facial data. The face detection can be based on using one or more classifiers for detecting the face. The classifiers can be trained to detect a partially occluded face that occurs on an image basis, that is, when only part of the face may be seen. But with appropriate classifiers, the partially occluded face can still be analyzed. The performing face detection can be used to identify an occupant of the vehicle. The identifying the occupant of the vehicle can be based on facial recognition. The flow 100 further includes filtering out faces 114 of one or more other people to determine whether the occupant of a vehicle is looking toward the camera. The occupant who may be looking toward the camera can be the operator of the vehicle, a passenger within the vehicle, and so on. The filtering out faces can be used for cognitive state analysis of the individual based on data collected when the individual is looking toward the camera.

The flow 100 further comprises collecting audio data 120 and augmenting the cognitive state data with the audio data. The audio data can augment the cognitive state data including facial data. The audio data can include ambient audio collected within the vehicle, "road noise" data collected from sources outside the vehicle, and the like. In embodiments, the audio data includes voice data. The voice data can include voice data from the operator of the vehicle, voice data from one or more passengers within the vehicle, voice data from an audio source within the vehicle, where the audio source can include a radio, an audio system, etc. The flow 100 further includes evaluating the voice data 122 for timbre, prosody, vocal register, vocal resonance, pitch, loudness, speech rate, or language content. The evaluating the voice data can include devaluating for cognitive states such as happy, sad, angry, bored, and the like. In embodiments, the voice data includes non-speech vocalizations. The non-speech vocalizations can occur contemporaneously with facial image events. In embodiments, the non-speech vocalizations can include grunts, yelps, squeals, snoring, sighs, laughter, filled pauses, unfilled pauses, or yawns. The audio data can provide cognitive state data to augment image data that includes a partially occluded face. The audio data can originate from the occupant whose face is occluded, or from other occupants, and be analyzed accordingly. In embodiments, the audio data enables analyzing cognitive state data for the face that is partially occluded.

The flow 100 further includes collecting other cognitive state data 124 from the occupant of a vehicle on a continuous basis. The other cognitive state data can include further facial data, further audio data, and so on. The other cognitive state data can include physiological data, accelerometer data, and the like. In embodiments, the cognitive state data can include one or more of a group including physiological data, facial data, or accelerometer data. As discussed, the audio data can include both speech data and non-speech vocalizations. The physiological data can include one or more of electrodermal activity, heart rate, heart rate variability, skin temperature, or respiration. The collecting cognitive state data, including other cognitive state data can be intermittent. In embodiments, the facial image data, audio data, physiological data, etc., can be collected intermittently while the occupant of a vehicle is looking toward a camera. The flow 100 further includes interpolating cognitive state data 126 when the cognitive state data collected is intermittent. New cognitive state data points can be constructed between known (e.g. collected) cognitive state data points. The new cognitive state data points can be constructed using a variety of techniques including piecewise constant techniques, linear interpolation techniques, polynomial interpolation techniques, spline interpolation techniques, and so on.

The flow 100 includes cognitive state data, where the cognitive state data from multiple sources is tagged 130. The tagging of the cognitive state data can include tagging based on a video event, an audio event, an event related to the vehicle such as braking or acceleration, a traffic event such as a traffic jam, and so on. The tagging can be based on the occupant of the vehicle. In embodiments, the cognitive state data is tagged with an identity value for the occupant of a vehicle. The identity value of the occupant of the vehicle can be based on an identifier such as an occupant identification (ID). The identity value of the occupant can be based on a user login, facial recognition, etc. Tags can include various types of information including metadata related to the cognitive state data, the user being monitored, the device that captured the cognitive state data, or other types of data. The cognitive state data from multiple sources can be tagged with information identifying the source that captured the cognitive state data. In embodiments, the cognitive state data can be tagged with information on a context in which the cognitive state data was collected. The context can include operating a vehicle, riding in a vehicle, a facial expression, a vocalization, or the like. The flow 100 further includes partitioning the cognitive state data 140 based on tagging. The partitioning can include partitioning video data into video segments, audio data into audio segments, and so on. The partitioning can be based on events such as facial events, audio events, vehicle events, physiological events, and the like. The cognitive state data can be reassembled, based on the tagging, which allows the combination of images collected from multiple devices. Analysis of the tagged data can generate an emotigraphic profile for an individual. The partitioning can separate the cognitive state data into two or more groups depending on the contents of the tags.

The flow 100 includes generating, using a second computing device, analysis of the cognitive state data 150 which is collected from the multiple sources. In some embodiments, obtaining analysis includes performing the analysis on a local computer, which may be the computer that collected the cognitive state data and/or a computer with which a user being monitored is interacting. In some embodiments, the obtaining of analysis includes performing the analysis on a local server, a quasi-local server—for example, a server in the same building or campus as the user being monitored—or on a remote server, a distributed server, a cloud server, etc. In some embodiments, the obtaining analysis includes receiving the analysis from another computer, such as a local or remote server. The flow 100 further comprises analyzing occluded faces 151. The occultation of faces can occur on a time basis or an image basis. Any combination of occultation can occur, including simultaneous time- and image-bases occultation. In such cases, combined intermittent image analysis, partial-face classifier analysis, and audio data analysis can be performed to determine cognitive state data for the occluded face. Additionally, a partial occlusion can be so near complete that it can be considered to be fully occluded, and hence the term "partial occlusion" includes the case of "full occlusion" for purposes of understanding the concepts described herein.

In some embodiments, the analysis of the cognitive state data is obtained from a web service. Because the cognitive state data can be collected using multiple sources, the analysis can include aggregating the cognitive state data 152 from the multiple sources. Cognitive state data can be stitched together from the various sources and the stitching may occur at a web service. Stitching can include using cognitive state data, or analysis from the cognitive state data, from multiple sources to provide a more complete picture of the cognitive experiences, emotional experiences, etc., of the individual. In some embodiments, analysis includes identifying a best view where two or more of the multiple sources have a camera with a view of the individual. Cognitive state data from the best view may be used or given priority in the obtaining of the analysis. The best view, in most cases the front view of the face, is then used in cognitive state analysis. Aggregating the cognitive state data can provide for analysis to occur even when a face is occluded or partially occluded. In embodiments, the aggregating enables analyzing cognitive state data for the face that is partially occluded.

The flow 100 further comprises interpolating cognitive state analysis 154 where the cognitive state data collected is intermittent. In some embodiments, the interpolating can be performed between data sets collected from the plurality of cognitive data sources. The interpolating can generate interpolated data for time periods during which cognitive state data was not collected from one or more of the multiple sources. The flow may include assembling the cognitive state data from the multiple sources at a web service, analyzing the cognitive state data to provide cognitive state information, and using the cognitive state information, based on the cognitive state data from the multiple sources, to infer cognitive states. The flow 100 further comprises imputing 156 additional cognitive state data for one or more periods where no cognitive state data was collected. The imputing can include filling in blanks where data has not been collected, interpolating between points in time where data has been collected, extrapolating from a previously collected data point, or the like. Analysis, based on the multiple sources of cognitive state data, can be used in market research. In some cases, an advertisement can be sent to an individual on a specific device, based on data obtained from that device and other devices. Using the multiple devices, a neutral cognitive state can be determined from one device and an advertisement or other media presentation can be sent to that or another device. Further, a specific cognitive state or emotional state can be targeted and anticipated across the various devices. When that cognitive state is detected, an advertisement or media presentation can be sent to a desired device. Analysis that is based on the multiple sources of cognitive state data can be used to manipulate a vehicle. The vehicle can be an autonomous vehicle, a semi-autonomous vehicle, and the like. The manipulation of the vehicle can include braking, acceleration, steering, navigation, etc. Control of the vehicle can be transferred from the individual to the autonomous or semi-autonomous vehicle. Control of the vehicle can be transferred from the vehicle to the occupant of the vehicle.

The flow 100 further comprises partitioning the cognitive state data 158 based on both the additional cognitive state data that was imputed and the tagging. After the additional cognitive state data is generated through imputation, tags can be added or updated to include various types of information including metadata related to the imputed cognitive state data, the user being monitored, the device that captured the original cognitive state data, or other types of data. The cognitive state data from multiple sources can be tagged with information identifying the source that captured the cognitive state data. The cognitive state data and the imputed additional cognitive state data can be tagged with an identity value for the individual. The cognitive state data and the imputed additional cognitive state data can be reassembled, based on the tagging, allowing the combination of images collected from multiple devices. Analysis of the tagged data can allow the generation of an emotigraphic profile for an individual. The cognitive state data can be tagged with information on the context in which the cognitive state data was collected. The partitioning can separate the cognitive state data and the additional cognitive state data into two or more groups depending on the contents of the tags.

The flow 100 further comprises inferring cognitive states 160 based on the cognitive state data which was collected. One or more cognitive states can be inferred from the facial image data, the audio data, or the physiological data. The one or more cognitive states that may be inferred can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state data can include information based on the Facial Action Coding System (FACS). FACS is a detailed catalog of unique action units that correspond to independent motions of the face. FACS enables the measurement and scoring of facial activity in an objective, reliable, and quantitative way, and can be used to discriminate between subtle differences in facial motion. Various independent motions can be classified using action units; in embodiments, the cognitive state data includes FACS action units. The cognitive state data can include one or more of head position, up/down head motion, side-to-side head motion, tilting head motion, body leaning motion, or gaze direction. Various cognitive states can be inferred, and the cognitive states can comprise one or more of a group including frustration, confusion, disappointment, hesitation, cognitive overload, focusing, being engaged, attending, boredom, exploration, confidence, trust, delight, or satisfaction.

The flow 100 further comprises determining contextual information 162. The contextual information can be related to the collected cognitive state data. A variety of types of contextual information related to the collection of the cognitive state data can be obtained. Some examples of collectable contextual information include a task assigned to the user, the location of the user, the environ-cognitive conditions that the user is exposed to—such as temperature, humidity, and the like—the name of the content being viewed, the level of noise experienced by the user, or any other type of contextual information. In some embodiments, the contextual information is based on one or more of skin temperature, accelerometer data, a photograph, an email, a text message, a phone log, or GPS information. The flow 100 further comprises populating a calendar 164 based on the cognitive states which were inferred. The populating the calendar can include placing cognitive state data, cognitive state information, or representations of cognitive states in a timeline or calendar for a viewer's benefit or review. The populating the calendar can show the range of cognitive states experienced by an individual over a period of time. The populating the calendar can show the number of days the individual met a goal such as to be happy, not to be angry, to concentrate, etc.

The flow 100 includes rendering, on a third computing device, an output 170 based on the analysis of the cognitive state data. In various embodiments, the rendering can be visual, where the rendering can be rendered on a display within the vehicle, on a remote display, on a display coupled to a mobile device, or the like. The rendering can be graphical, pictorial, textual, or any combination thereof. The rendering can be auditory, where the rendering is played through an audio system or a mobile device, presented as a bell or alarm, etc. The rendering can include an emotigraphic profile. In some embodiments the rendering is printed on paper. The flow 100 further comprises posting information based on the analysis to a social network page 172. The posting can include images, videos, text, and so on. The social network page can include a personal page or a group page. The posting to the social network page can include an emoji, an animated emoji, a graphic interchange format (GIF), a cartoon, an avatar, etc. In embodiments, the rendering can be used to provide vehicle performance data to one or more occupants of the vehicle. The vehicle performance data can include speed, distance, mileage, miles-per-gallon, fuel remaining, engine temperature, oil pressure, and so on. In embodiments, the rendering can be used to provide vehicle control to one or more occupants of the vehicle. As discussed elsewhere, control can be transferred from the occupant to the vehicle or from the vehicle to the occupant, based on the cognitive state analysis that is generated.

The flow 100 can include cognitive state analysis comprising: obtaining, on a first computing device, cognitive state data which is collected on an occupant of a vehicle from multiple sources, wherein the multiple sources include at least two sources of facial image data; generating, using a second computing device, analysis of the cognitive state data which is collected from the multiple sources; and providing, to a third computing device, the analysis 174 of the cognitive state data. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
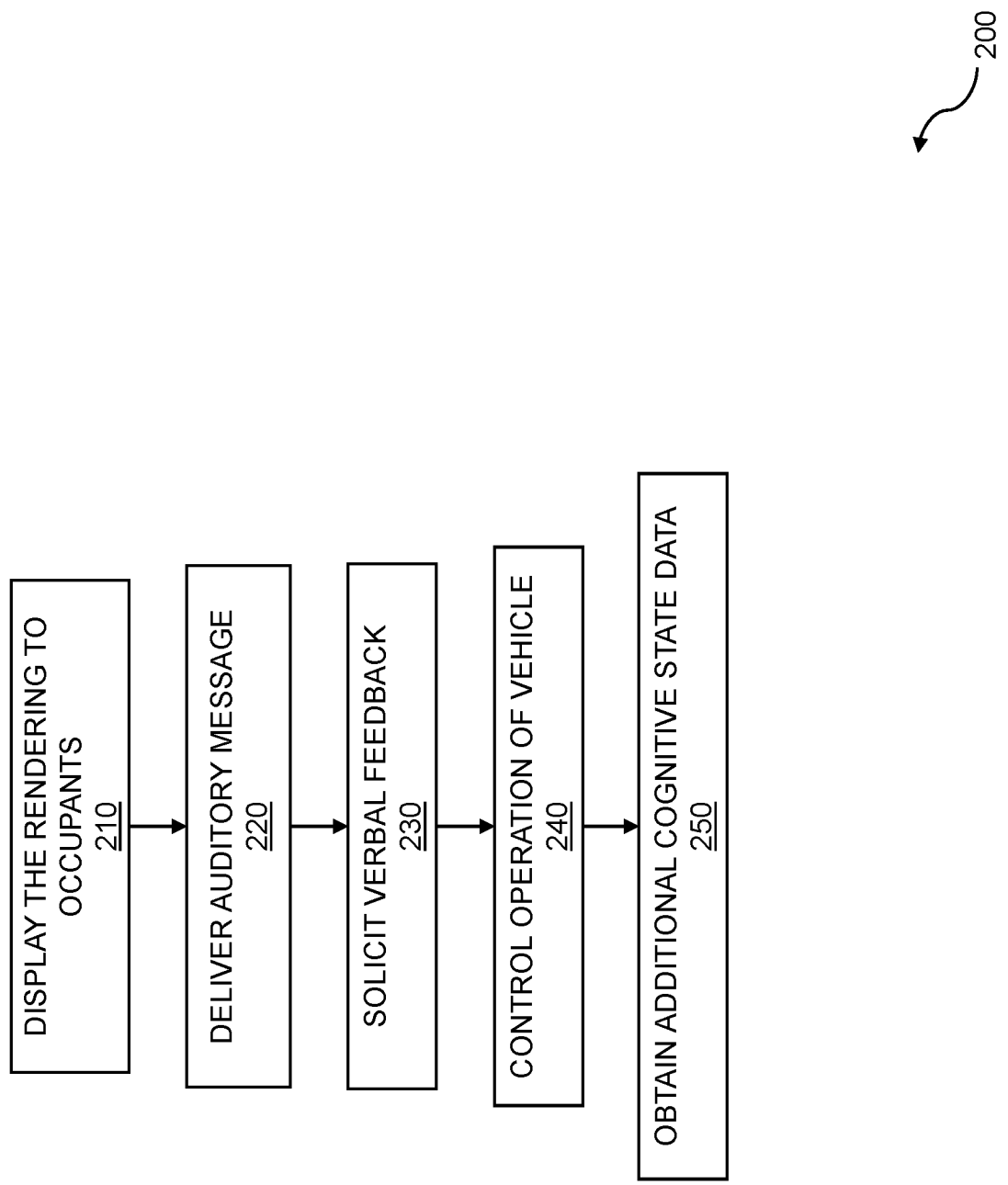
FIG. 2 is a flow diagram for controlling vehicle operation based partially on audio feedback.

FIG. 2 is a flow diagram for controlling vehicle operation based partially on audio feedback. Vehicular cognitive data collection uses multiple devices to collect cognitive state data on an occupant of the vehicle. The collected cognitive state data is collected from multiple sources, where at least two sources include facial image data. Other sources for collecting cognitive state data can include sources of audio data such as voice data, sources of physiological data, and so on. Analysis of the cognitive state data is generated, and an output based on the analysis is rendered. The flow 200 includes displaying the rendering in visual format to one or more occupants 210 of the vehicle. The rendering that can be displayed can include a graphical display, an image, an animation, an emoji, an animated emoji, a video clip of one or more occupants of the vehicle, an avatar, and so on. In embodiments, the rendering can visual. The visual rendering can include a flashing light, an animated icon, a video clip, and so on. The rendering can be displayed on a screen within the vehicle, on a mobile device within the vehicle, on a "heads up" display, on a projector, and the like. The flow 200 includes delivering an auditory message 220 complementing the rendering, where the auditory message provides clarification of the rendering. In embodiments the rendering can be auditory. The auditory message can include a prerecorded message, a synthesized message, a warning, an alarm, a query, etc. A usage example can include displaying a rendering of a map showing traffic and delivering an auditory message warning of traffic or an accident ahead, suggesting an alternative route to avoid the traffic, and so on.

The flow 200 includes soliciting, using a digital voice, verbal feedback 230 from a primary occupant of the vehicle. The primary occupant can be the operator of the vehicle, the sole occupant of the vehicle, a passenger within the vehicle, etc. The digital voice can be played through an audio system within the vehicle, played on a mobile device, and so on. Continuing the usage example, the digital voice can be used to provide more than one alternative route to avoid traffic or an accident, and then to query the operator of the vehicle to select which route she or he would like to choose. The flow 200 includes controlling the operation of the vehicle 240 based on the verbal feedback that was solicited and the analysis of the cognitive state data. In embodiments, the controlling the operation of the vehicle can include transferring operation of the vehicle from the occupant to the vehicle, where the vehicle can be an autonomous vehicle or a semiautonomous vehicle. The autonomous operation or semiautonomous vehicle operation can include brake activation, throttle activation, or steering control. In other embodiments, the controlling operation of the vehicle can include transferring operation of the vehicle from autonomous operation mode or semiautonomous mode operation to operation by the occupant. The cognitive state of the occupant of the vehicle can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

The flow 200 further includes obtaining additional cognitive state data 250 based on the controlling the operation of the vehicle. The additional cognitive state data can include image data, facial data, audio data, voice data, speech data, non-speech vocalizations, physiological data, and so on. In embodiments, the physiological data can include one or more of electrodermal activity, heart rate, heart rate variability, skin temperature, or respiration. Various steps in the flow 200 may be changed in order, repeated, omitted, or the like without departing from the disclosed concepts. Various embodiments of the flow 200 may be included in a computer program product embodied in a non-transitory computer readable medium that includes code executable by one or more processors.

Figure 3:
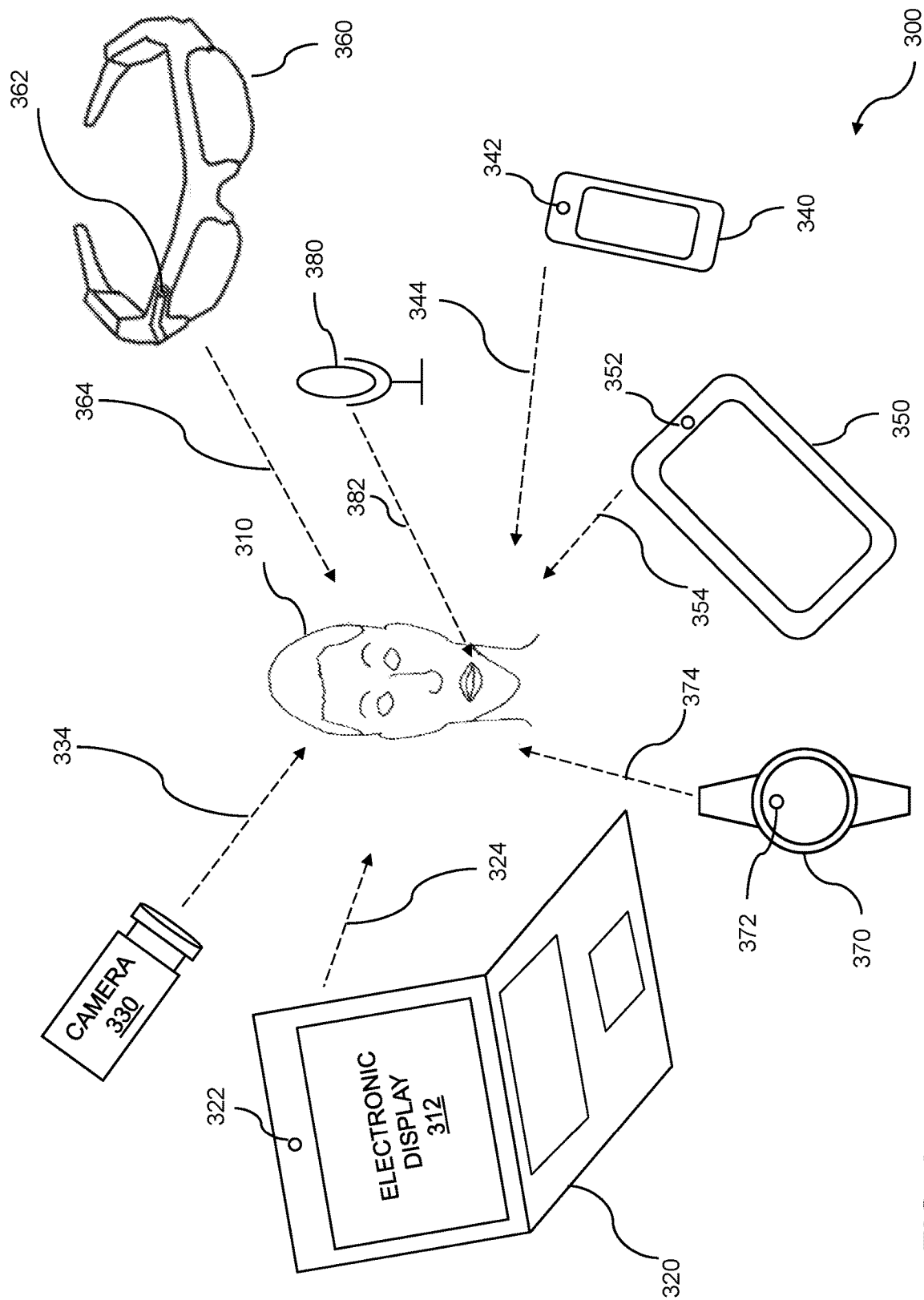
FIG. 3 shows example image and audio collection including multiple mobile devices.

FIG. 3 shows example image and audio collection including multiple mobile devices. Cognitive state data which can include facial image data, voice data, physiological data, or the like, can be collected using multiple mobile devices. The collected cognitive state data can be based on vehicular cognitive data collection using multiple devices. The cognitive state data which is collected on an occupant of the vehicle can be obtained from multiple sources. Analysis of the cognitive state data which is collected from the multiple sources is generated, and an output is rendered based on the analysis of the cognitive state data. While one person is shown, in practice the video data, audio data, physiological data, etc., can be collected on any number of people. In the diagram 300, the multiple mobile devices can be used separately or in combination to collect video data, audio data, or both video data and audio data on a user 310. While one person is shown, the video data and audio data can be collected on multiple people. A user 310 can be observed as she or he is performing a task, experiencing an event, viewing a media presentation, and so on. The user 310 can be shown one or more media presentations, political presentations, social media, or another form of displayed media. The one or more media presentations can be shown to a plurality of people. The media presentations can be displayed on an electronic display 312 or another display. The data collected on the user 310 or on a plurality of users can be in the form of one or more videos, video frames, still images, one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations and viewing either a single media presentation or a plurality of presentations. The data collected on the user 310 can be analyzed and viewed for a variety of purposes including expression analysis, cognitive state analysis, mental state analysis, emotional state analysis, and so on. The electronic display 312 can be on a laptop computer 320 as shown, a tablet computer 350, a cell phone 340, a television, a mobile monitor, or any other type of electronic device. In one embodiment, video data including expression data is collected on a mobile device such as a cell phone 340, a tablet computer 350, a laptop computer 320, or a watch 370. Similarly, the audio data including voice data and non-speech vocalizations can be collected on one or more of the mobile devices. Thus, the multiple sources can include at least one mobile device, such as a phone 340 or a tablet 350, or a wearable device such as a watch 370 or glasses 360. A mobile device can include a front-side camera and/or a back-side camera that can be used to collect expression data. A mobile device can include a microphone, audio transducer, or other audio capture apparatus that can be used to capture the speech and non-speech vocalizations. Sources of expression data can include a webcam 322, a phone camera 342, a tablet camera 352, a wearable camera 362, and a mobile camera 330. A wearable camera can comprise various camera devices, such as a watch camera 372. Sources of audio data 382 can include a microphone 380.

As the user 310 is monitored, the user 310 might move due to the nature of the task, boredom, discomfort, distractions, or for another reason. As the user moves, the camera with a view of the user's face can be changed. Thus, as an example, if the user 310 is looking in a first direction, the line of sight 324 from the webcam 322 is able to observe the user's face, but if the user is looking in a second direction, the line of sight 334 from the mobile camera 330 is able to observe the user's face. Furthermore, in other embodiments, if the user is looking in a third direction, the line of sight 344 from the phone camera 342 is able to observe the user's face, and if the user is looking in a fourth direction, the line of sight 354 from the tablet camera 352 is able to observe the user's face. If the user is looking in a fifth direction, the line of sight 364 from the wearable camera 362, which can be a device such as the glasses 360 shown and can be worn by another user or an observer, is able to observe the user's face. If the user is looking in a sixth direction, the line of sight 374 from the wearable watch-type device 370, with a camera 372 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 310 can also use a wearable device including a camera for gathering contextual information and/or collecting expression data on other users. Because the user 310 can move her or his head, the facial data can be collected intermittently when she or he is looking in a direction of a camera. In some cases, multiple people can be included in the view from one or more cameras, and some embodiments include filtering out faces of one or more other people to determine whether the user 310 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capturing device.

Figure 4:
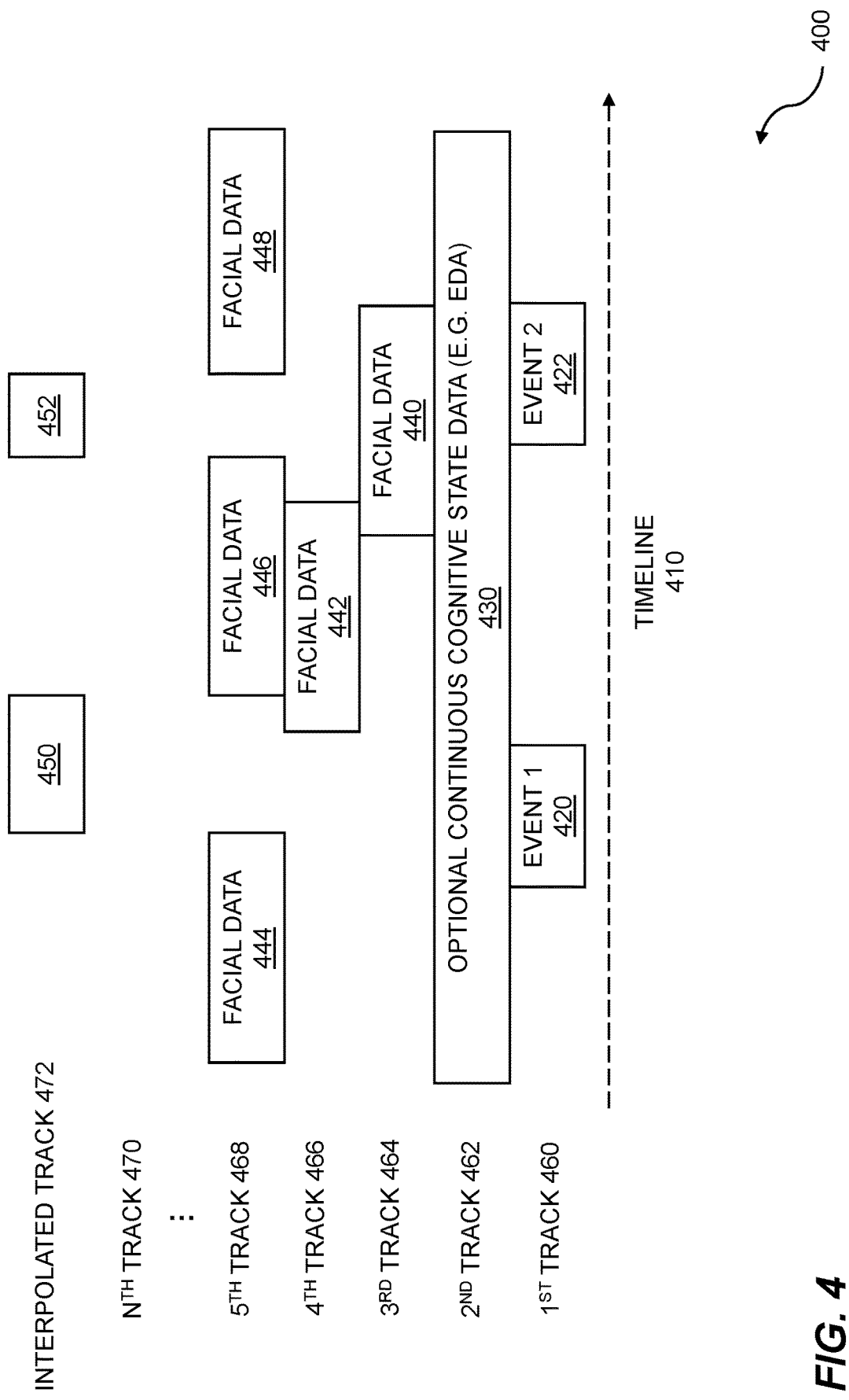
FIG. 4 is a timeline with information tracks relating to cognitive states.

FIG. 4 is a timeline with information tracks relating to cognitive states. A timeline can show cognitive states based on vehicular cognitive data collection using multiple devices. Cognitive state data which is collected on an occupant of the vehicle is obtained from multiple sources. The multiple sources include two or more sources of facial image data, and can include sources of speech data, physiological data, and so on. Analysis of the cognitive state data is generated. An output is rendered based on the analysis of the cognitive state data.

The timeline 410 with information tracks 400 relates to various cognitive states. A first track 460 shows events that, in embodiments, are related to use of a computer by the individual. A first event 420 can indicate an action that the individual took (such as launching an application); an action initiated by the computer (such as the presentation of a dialog box); an external event (such as a new global positioning system (GPS) coordinate); or another event such as receiving an e-mail, a phone call, a text message, or any other type of event. In some embodiments, a photograph can be used to document an event or simply to save contextual information in the first track 460. A second event 422 can indicate another action or event in a similar manner. Such events can be used to provide contextual information and can also include information such as copies of emails, text messages, phone logs, file names, or other information that can prove useful in understanding the context of a user's actions. Thus, in embodiments, contextual information is based on one or more of a photograph, an email, a text message, a phone log, or GPS information.

A second track 462 can include continuously collected cognitive state data such as electrodermal activity data 430. A third track 464 can include facial data, which, in embodiments, is a type of cognitive state data that is collected on an intermittent basis by a first camera, such as the room mobile camera 330 of FIG. 3 (although in some embodiments the facial data is collected continuously). The facial data can be collected intermittently when the individual is looking toward a camera. The facial data 440 can include one or more still photographs, videos, or abstracted facial expressions which can be collected when the user looks in the direction of the camera. A fourth track 466 can include facial data that is collected on an intermittent or continuous basis by a second camera, such as the mobile phone camera 342 of FIG. 3. The facial data 442 can include one or more still photographs, videos, or abstracted facial expressions which can be collected when the user looks in the direction of that camera. A fifth track 468 can include facial data that is collected from a third camera, such as the webcam 322 of FIG. 3. In the example shown, the fifth track 468 includes first facial data 444, second facial data 446, and third facial data 448, which can be any type of facial data including data that can be used for determining cognitive state information. Any number of samples of facial data can be collected in any track. The cognitive state data from the various tracks can be collected simultaneously, collected on one track exclusive of other tracks, collected where cognitive state data overlaps between the tracks, and so on. When cognitive state data from multiple tracks overlap, one track's data can take precedence or the data from the multiple tracks can be combined.

Additional tracks, through the $n^{th}$ track 470, of cognitive state data of any type can be collected. The additional tracks can be collected on a continuous or on an intermittent basis. The intermittent basis can be either occasional or periodic. Analysis can further comprise interpolating cognitive state data when the cognitive state data collected is intermittent, and/or imputing additional cognitive state data where the cognitive state data is missing. One or more interpolated tracks 472 can be included and can be associated with cognitive state data that is collected on an intermittent basis, such as the facial data of the fifth track 468. Interpolated data 450 and interpolated data 452 can contain interpolations of the facial data of the fifth track 468 for the time periods where no facial data was collected in that track. Other embodiments interpolate data for periods where no track includes facial data. In other embodiments, analysis includes interpolating cognitive state analysis when the cognitive state data collected is intermittent.

The cognitive state data, such as the continuous cognitive state data 430 and/or any of the collected facial data 440, 442, 444, 446, and 448, can be tagged. The tags can include metadata related to the cognitive state data, including, but not limited to, the device that collected the cognitive state data; the individual from whom the cognitive state data was collected; the task being performed by the individual; the media being viewed by the individual; and the location, environ-cognitive conditions, time, date, or any other contextual information. The tags can be used to locate pertinent cognitive state data; for example, the tags can be used to retrieve the cognitive state data from a database. The tags can be included with the cognitive state data that is sent over the internet to cloud or web-based storage and/or services; so, the tags can be used locally on the machine where the cognitive state data was collected and/or remotely on a remote server or a cloud/web service.

Figure 5:
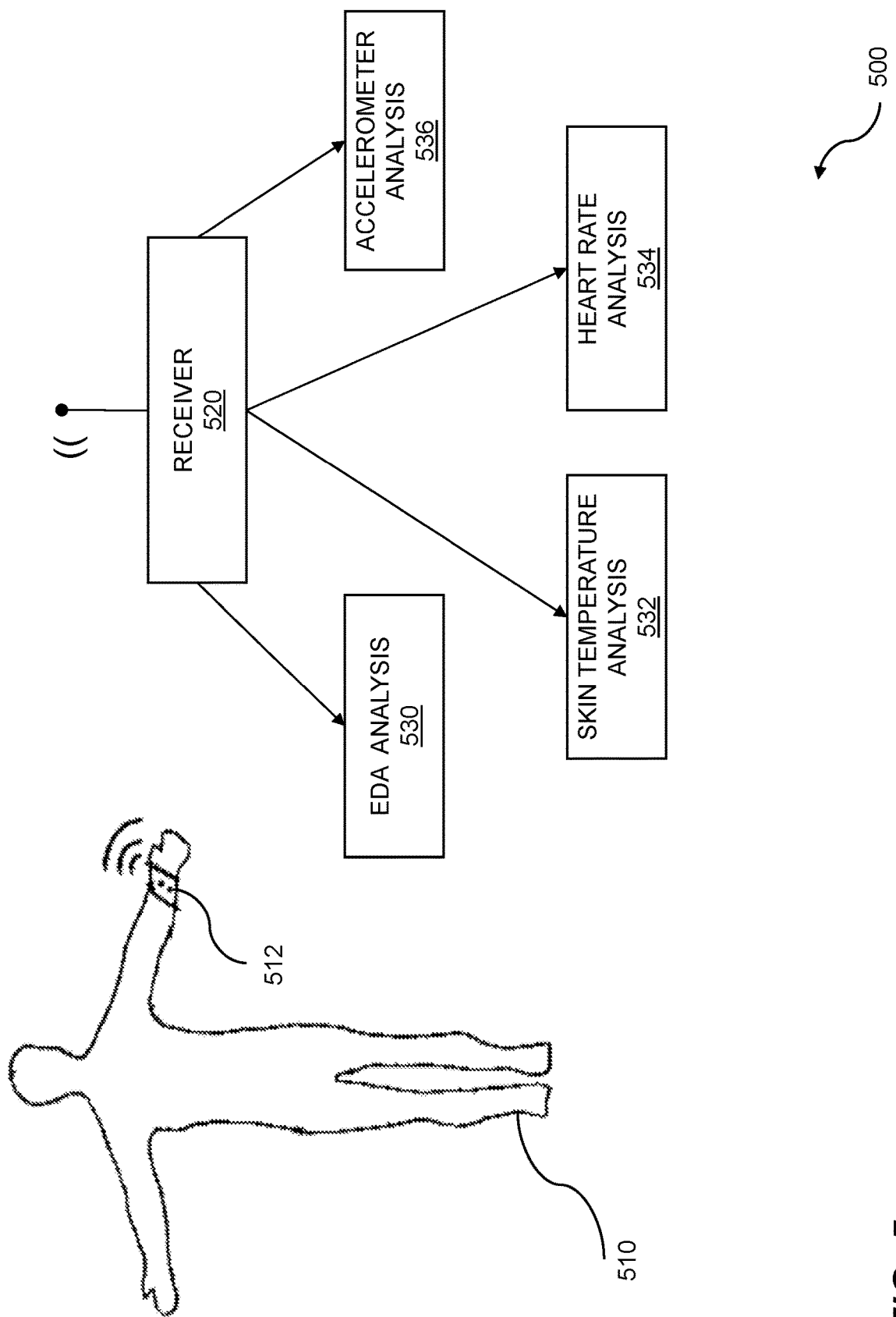
FIG. 5 is diagram for sensor analysis.

FIG. 5 is diagram for sensor analysis. One or more sensors can be used for vehicular cognitive data collection using multiple devices. The sensors can include a camera, a microphone, a motion sensor, and accelerometer, and so on. The sensors can be within a vehicle, in sight of the vehicle, etc. Cognitive state data which is collected on an occupant of the vehicle is obtained from multiple sources. The sources can include the sensors. The sources can include video data, facial data, audio data, speech data, physiological data, and the like. Analysis of the cognitive state data is generated, and an output is rendered.

A system 500 can analyze data collected from a person 510 as she or he interacts with a computer or views a media presentation. The person 510 can have a biosensor 512 attached to him or her for the purpose of collecting cognitive state data. The biosensor 512 can be placed on the wrist, palm, hand, head, or other part of the body. In some embodiments, multiple biosensors are placed on the body in multiple locations. The biosensor 512 can include detectors for physiological data such as electrodermal activity, skin temperature, accelerometer readings, and the like. Other detectors for physiological data can also be included, such as heart rate, blood pressure, EKG, EEG, other types of brain waves, and other physiological detectors. The biosensor 512 can transmit collected information to a receiver 520 using wireless technology such as Wi-Fi™, Bluetooth™, 802.11, cellular, Zigbee™, or other bands. In other embodiments, the biosensor 512 communicates with the receiver 520 using other methods such as a wired or optical interface. The receiver can provide the data to one or more components in the system 500. In some embodiments, the biosensor 512 records multiple types of physiological information in memory for later download and analysis. In some embodiments, the download of recorded physiological data is accomplished through a USB port or other form of wired or wireless connection.

Cognitive states can be inferred based on physiological data, such as physiological data from the sensor 512. Cognitive states can also be inferred based on facial expressions and head gestures observed by a webcam or by using a combination of data from the webcam and data from the sensor 512. The cognitive states can be analyzed based on arousal and valence. Arousal can range from being highly activated, such as when someone is agitated, to being entirely passive, such as when someone is bored. Valence can range from being very positive, such as when someone is happy, to being very negative, such as when someone is angry. Physiological data can include one or more of electrodermal activity (EDA), heart rate, heart rate variability, skin temperature, respiration, accelerometer readings, and other types of analysis of a human being. It will be understood that both here and elsewhere in this document physiological information can be obtained either by biosensor 512 or by facial observation via an image capturing device. Facial data can include facial actions and head gestures used to infer cognitive states. Further, the data can include information on hand gestures or body language and body movements such as visible fidgets. In some embodiments, these movements are captured by cameras, while in other embodiments, these movements are captured by sensors. Facial data can include the tilting the head to the side, leaning forward, smiling, frowning, and many other gestures or expressions.

In some embodiments, electrodermal activity is collected, either continuously, every second, four times per second, eight times per second, 32 times per second, or on some other periodic basis. Or, in some embodiments, electrodermal activity is collected on an intermittent basis. The electrodermal activity can be recorded and stored onto a disk, a tape, flash memory, a computer system, or streamed to a server. The electrodermal activity can be analyzed 530 to indicate arousal, excitement, boredom, or other cognitive states based on observed changes in skin conductance. Skin temperature can be collected and/or recorded on a periodic basis. In turn, the skin temperature can be analyzed 532. Changes in skin temperature can indicate arousal, excitement, boredom, or other cognitive states. Heart rate information can be collected/recorded and can also be analyzed 534. A high heart rate can indicate excitement, arousal, or other cognitive states. Accelerometer data can be collected and used to track one, two, or three dimensions of motion. The accelerometer data can be recorded. The accelerometer data can be used to create an actigraph showing an individual's activity level over time. The accelerometer data can be analyzed 536 and can indicate a sleep pattern, a state of high activity, a state of lethargy, or other states. The various data collected by the biosensor 512 can be used along with the facial data captured by the webcam in the analysis of cognitive states. Contextual information can be based on one or more of skin temperature and/or accelerometer data. The cognitive state data can include one or more of a group including physiological data, facial data, and accelerometer data.

Figure 6:
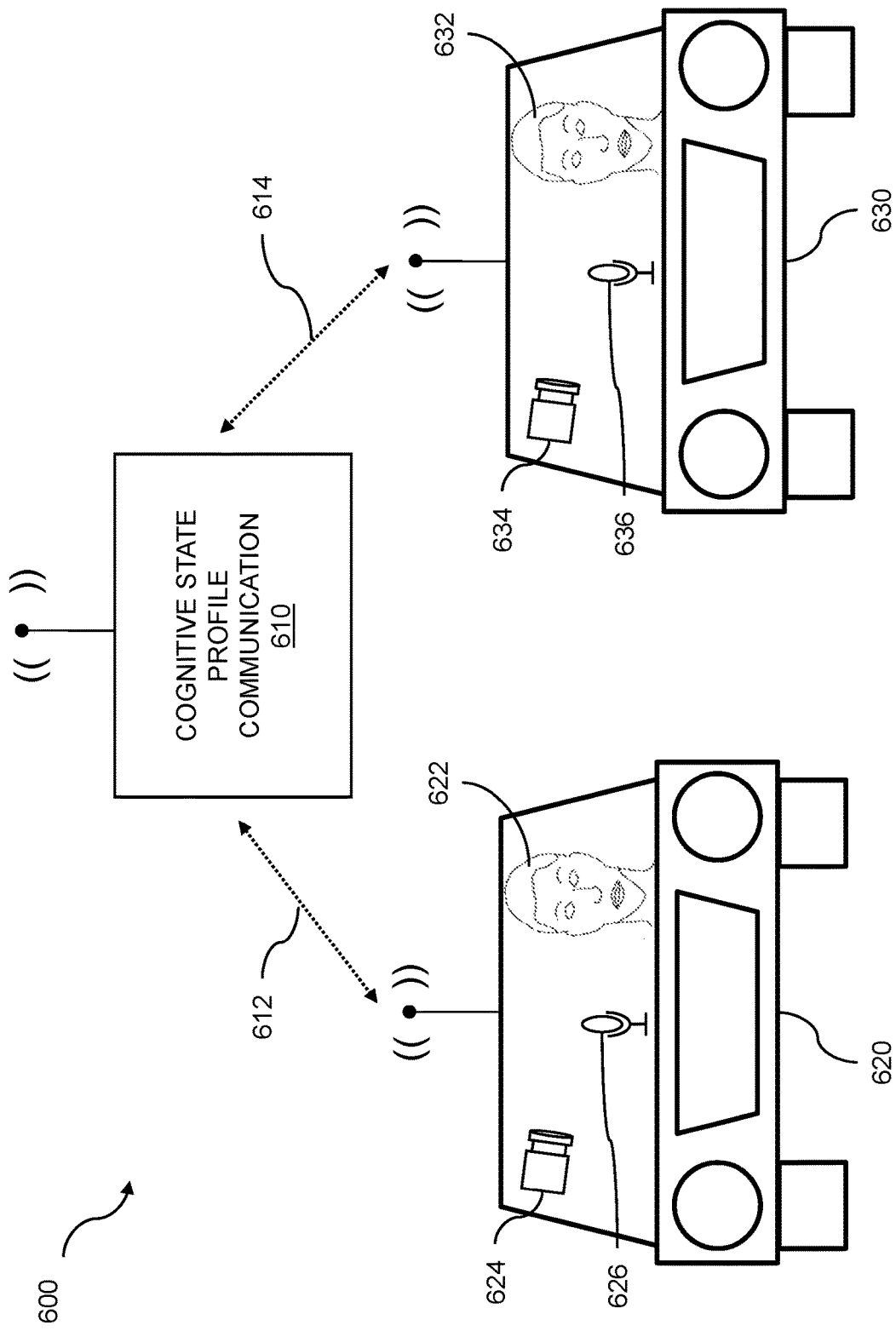
FIG. 6 is a system diagram for vehicle manipulation.

FIG. 6 is a system diagram for vehicle manipulation. Vehicle manipulation can include cognitive state analysis, where the cognitive state analysis can be based on vehicular cognitive data collection using multiple devices. A first computing device within a vehicle is used to obtain cognitive state data which is collected on an occupant of the vehicle. The cognitive state data is collected from multiple sources, where the multiple sources include at least two sources of facial image data. The multiple sources can include a source of audio data such as voice data. A second computing device generates analysis of the cognitive state data which is collected from the multiple sources. A third computing device renders an output which is based on the analysis of the cognitive state data.

A system diagram for vehicle manipulation 600 is shown. The system can include cognitive state profile communication 610. The communicating of the cognitive state profile communication can include sending cognitive state profile information to a first vehicle 620, to a second vehicle 630, and so on. The cognitive state profile communication can include manipulating the first vehicle 620, the second vehicle 630, etc. The manipulating can include a locking out operation; recommending a break for the occupant; recommending a different route; recommending how far to drive; responding to traffic; adjusting seats, mirrors, climate control, lighting, music, audio stimuli, interior temperature for the second vehicle; brake activation; steering control; and other vehicle control and manipulation techniques.

The cognitive state profile can be sent to a first vehicle 620 using a wireless link 612 or other data transfer technique. The cognitive state profile that can be sent can be based on cognitive state data including facial data from an occupant 622 of the vehicle 620. The cognitive state data including facial data can be collected using a camera 624 or other image capture technique. The system 600 can include collecting voice data and augmenting the cognitive state data with the voice data. The voice data can be collected from the occupant 622 using a microphone 626 or other audio capture technique. The voice data can include audio data, where the audio data can include traffic sounds, road noise, music, news, ebooks, etc., that can be played by the occupant, and so on. The system 600 can include evaluating the voice data for timbre, prosody, vocal register, vocal resonance, pitch, loudness, speech rate, or language content. The evaluating the voice data can also be used in evaluating the cognitive state or states of the occupant 622 of the vehicle 620. In embodiments, the augmenting can be based on lexical analysis of the voice data that looks at sentiment. As for the first vehicle, the cognitive state profile can be sent to a second vehicle 630 using a wireless link 614 or other data transfer technique. The cognitive state profile can be based on cognitive state data including facial data from an occupant 632 of the vehicle 630, can be based on the cognitive state data including facial from the occupant 622 of the first vehicle 620, and so on. The cognitive state data including facial data can be collected using a camera 634 or other image capture technique. The system 600 can include collecting voice data from the occupant 632 using a microphone 636 or other audio capture technique.

Figure 7:
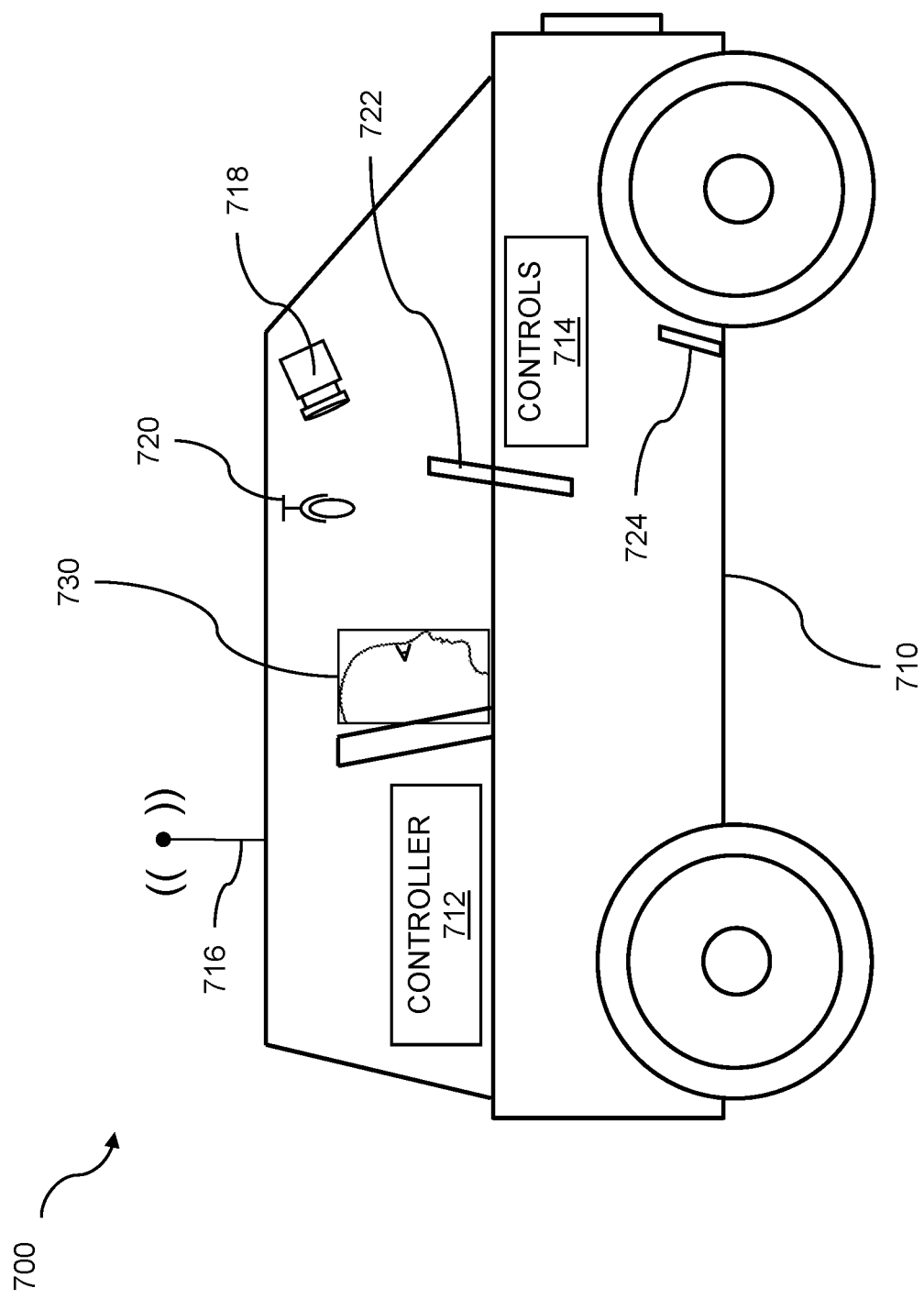
FIG. 7 is a system diagram for an interior of a vehicle.

FIG. 7 is a system diagram for an interior of a vehicle 700. Vehicular cognitive data collection uses multiple devices. Cognitive state data which is collected on an occupant of the vehicle is obtained from multiple sources. The multiple sources can include at least two sources of facial image data, a source of audio data such as speech data, and so on. Analysis of the cognitive state data which is collected from the multiple sources is generated, and an output is rendered based on the analysis. An occupant 730 of a vehicle 710 can be observed by using a camera 718, a microphone 720, and other image and audio capture techniques. The image data can include video data. The video data and the audio data can include cognitive state data, where the cognitive state data can include facial data, voice data, physiological data, and so on. The occupant can be a driver of the vehicle 710, a passenger within the vehicle, and so on.

The interior of a vehicle 710 can be a standard vehicle, an autonomous vehicle, a semi-autonomous vehicle, and so on. The vehicle can be an automobile, a van, a sport utility vehicle (SUV), a truck, a bus, a special purpose vehicle, a scooter, a chair, etc. The interior of the vehicle 710 can include standard controls such as a steering wheel 722, a throttle control (not shown), a brake 724, and so on. The interior of the vehicle can include other controls 714 such as controls for seats, mirrors, climate controls, an audio system, a video system, etc. The controls 714 of the vehicle 710 can be controlled by a controller 712. The controller 712 can control the vehicle 710 in various manners such as autonomously, semi-autonomously, assertively to a vehicle occupant 730, etc. In embodiments, the controller provides no vehicle control techniques, assistance, etc. The controller 712 can receive instructions via an antenna 716 or using other wireless techniques. The controller 712 can be pre-programmed to cause the vehicle to follow a specific route, to avoid traffic, to pull over, etc.

Figure 8:
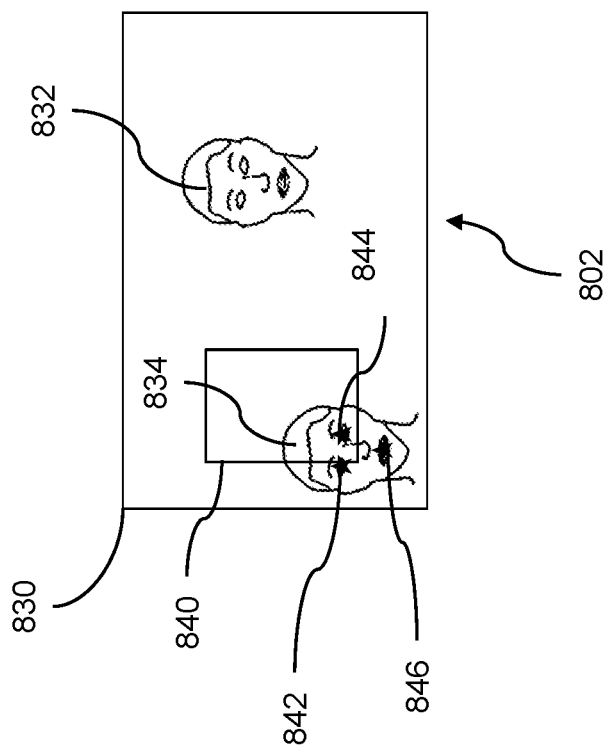
FIG. 8 illustrates feature extraction for multiple faces.
Figure 8:
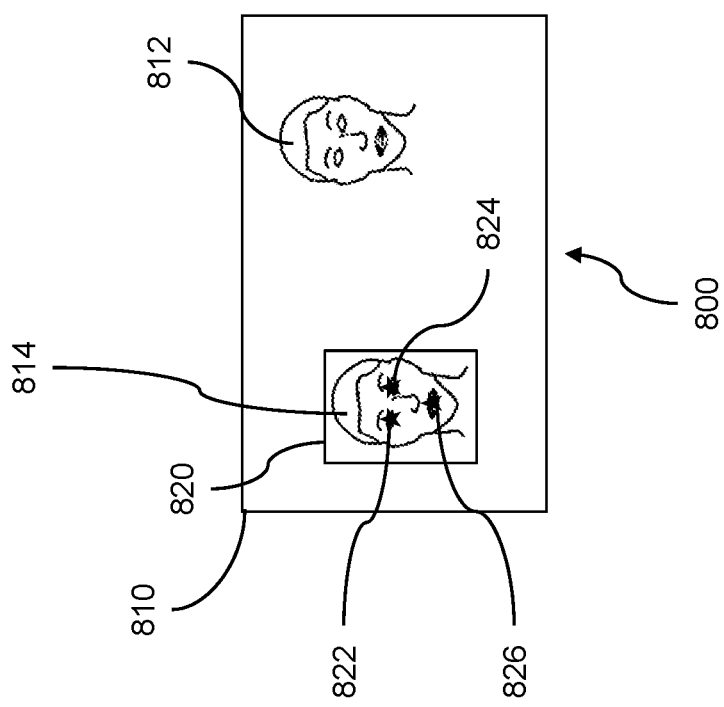

FIG. 8 illustrates feature extraction for multiple faces. Image analysis, including facial analysis, can be based on feature extraction from multiple faces. Vehicular cognitive data collection uses multiple devices. The vehicular cognitive data includes cognitive state data. Cognitive state data which is collected on an occupant of the vehicle is obtained from multiple sources. The multiple sources include at least two sources of facial image data and can include audio data such as voice data. Analysis is generated of the cognitive state data which is collected from the multiple sources. An output is rendered based on the analysis of the cognitive state data.

The feature extraction for multiple faces can be performed for faces that can be detected in multiple images. In embodiments, the features of multiple faces are extracted for evaluating cognitive states. Features of a face or a plurality of faces can be extracted from collected video data. The feature extraction can be performed by analysis, using one or more processors, using one or more video collection devices, and by using a server. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or existing observation, sample, datum, etc. should be placed. The decision to place an observation into a category can be based on training the algorithm or piece of code by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When a new observation is received, then the classifier can be used to categorize the new observation. Classifiers can be used for many analysis applications, including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables involving various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech, and handwriting recognition, and so on. Classification can be used for biometric identification of one or more people in a single frame or in multiple frames of one or more videos.

Returning to FIG. 8, the detection of the first face, the second face, and multiple faces can include identifying facial landmarks, generating a bounding box, and predicting of a bounding box and landmarks for a next frame, where the next frame can be one of a plurality of frames of a video containing faces. A first video frame 800 includes a frame boundary 810, a first face 812, and a second face 814. The video frame 800 also includes a bounding box 820. Facial landmarks can be generated for the first face 812. Face detection can be performed to initialize a second set of locations for a second set of facial landmarks for a second face within the video. Facial landmarks in the video frame 800 can include the facial landmarks 822, 824, and 826. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face and can include estimating a second rough bounding box for the second face based on the facial landmark detection. The estimating of a second rough bounding box can include the bounding box 820. Bounding boxes can also be estimated for one or more other faces within the boundary 810. The bounding box can be refined, as can one or more facial landmarks. The refining of the second set of locations for the second set of facial landmarks can be based on localized information around the second set of facial landmarks. The bounding box 820 and the facial landmarks 822, 824, and 826 can be used to estimate future locations for the second set of locations for the second set of facial landmarks in a future video frame from the first video frame.

A second video frame 802 is also shown. The second video frame 802 includes a frame boundary 830, a first face 832, and a second face 834. The second video frame 802 also includes a bounding box 840 and the facial landmarks, or points, 842, 844, and 846. In other embodiments, multiple facial landmarks are generated and used for facial tracking of the two or more faces of a video frame, such as the shown second video frame 802. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to differentiate between the first face and the second face, to track either the first face, the second face, or both faces, and so on. Other facial points can correspond to the second face. As mentioned above, multiple facial points can be determined within a frame. One or more of the other facial points that are determined can correspond to a third face. The location of the bounding box 840 can be estimated, where the estimating can be based on the location of the generated bounding box 820 shown in the first video frame 800. The three facial points shown, facial points, or landmarks, 842, 844, and 846, might lie within the bounding box 840 or might not lie partially or completely within the bounding box 840. For instance, the second face 834 might have moved between the first video frame 800 and the second video frame 802. Based on the accuracy of the estimating of the bounding box 840, a new estimation can be determined for a third, future frame from the video, and so on. The evaluation can be performed, all or in part, using semiconductor-based logic.

Figure 9:
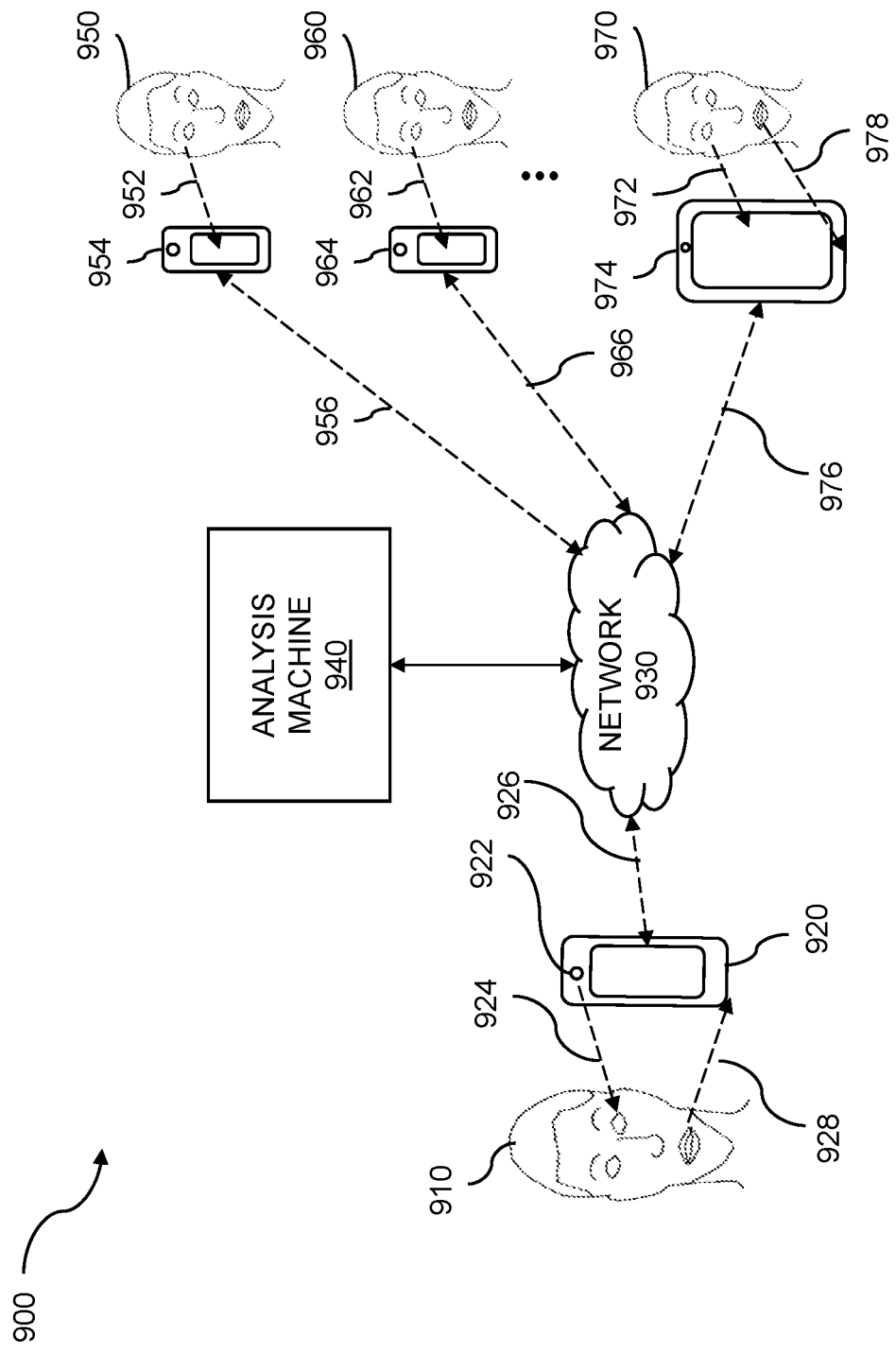
FIG. 9 shows an example of live streaming of social video and audio.

FIG. 9 shows an example of live streaming of social video and audio. The streaming of social video and social audio can be applied to vehicular cognitive data collection using multiple devices. The live streaming can include cognitive state data, image data, facial data, audio data, speech data, etc. The cognitive state data can be obtained on an occupant of a vehicle from multiple sources. The multiple sources can include at least two sources of facial image data. The multiple sources can include audio data such as speech data. Analysis of the cognitive state data is generated, and an output is rendered. The rendering can include providing an emotigraphic profile. The cognitive state data from the multiple sources can be tagged, where the cognitive state data can be tagged with an identity value for the occupant of the vehicle. The cognitive state data can be partitioned based on the tagging.

The live streaming and image analysis can be facilitated by a video capture device, a local server, a remote server, a semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcast as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen by and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 900 shows a user 910 broadcasting a video live stream and an audio live stream to one or more people as shown by a first person 950, a second person 960, and a third person 970. A portable, network-enabled, electronic device 920 can be coupled to a front-facing camera 922. The portable electronic device 920 can be a smartphone, a PDA, a tablet, a laptop computer, and so on. The camera 922 coupled to the device 920 can have a line-of-sight view 924 to the user 910 and can capture video of the user 910. The portable electronic device 920 can be coupled to a microphone (not shown). The microphone can capture voice data 928 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 940 using a network link 926 to the Internet 930. The network link can be a wireless link, a wired link, and so on. The recommendation engine 940 can recommend to the user 910 an app and/or platform that can be supported by the server and can be used to provide a video live stream, an audio live stream, or both a video live stream and an audio live stream to one or more followers of the user 910.

In the example 900, the user 910 has three followers: a first person 950, a second person 960, and a third person 970. Each follower has a line-of-sight view to a video screen on a portable, networked electronic device. In other embodiments, one or more followers follow the user 910 using any other networked electronic device, including a computer. In the example 900, a first person 950 has a line-of-sight view 952 to the video screen of a device 954; a second person 960 has a line-of-sight view 962 to the video screen of a device 964, and a third person 970 has a line-of-sight view 972 to the video screen of a device 974. The device 974 can also capture audio data 978 from the third person 970. The portable electronic devices 954, 964, and 974 can each be a smartphone, a PDA, a tablet, and so on. Each portable device can receive the video stream and the audio stream being broadcast by the user 910 through the Internet 930 using the app and/or platform that can be recommended by the recommendation engine 940. The device 954 can receive a video stream and the audio stream using the network link 956, the device 964 can receive a video stream and the audio stream using the network link 966, the device 974 can receive a video stream and the audio stream using the network link 976, and so on. The network link can be a wireless link, a wired link, a hybrid link, and so on. Depending on the app and/or platform that can be recommended by the recommendation engine 940, one or more followers, such as the followers shown 950, 960, and 970, can reply to, comment on, or otherwise provide feedback to the user 910 using their respective devices 954, 964, and 974.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 10:
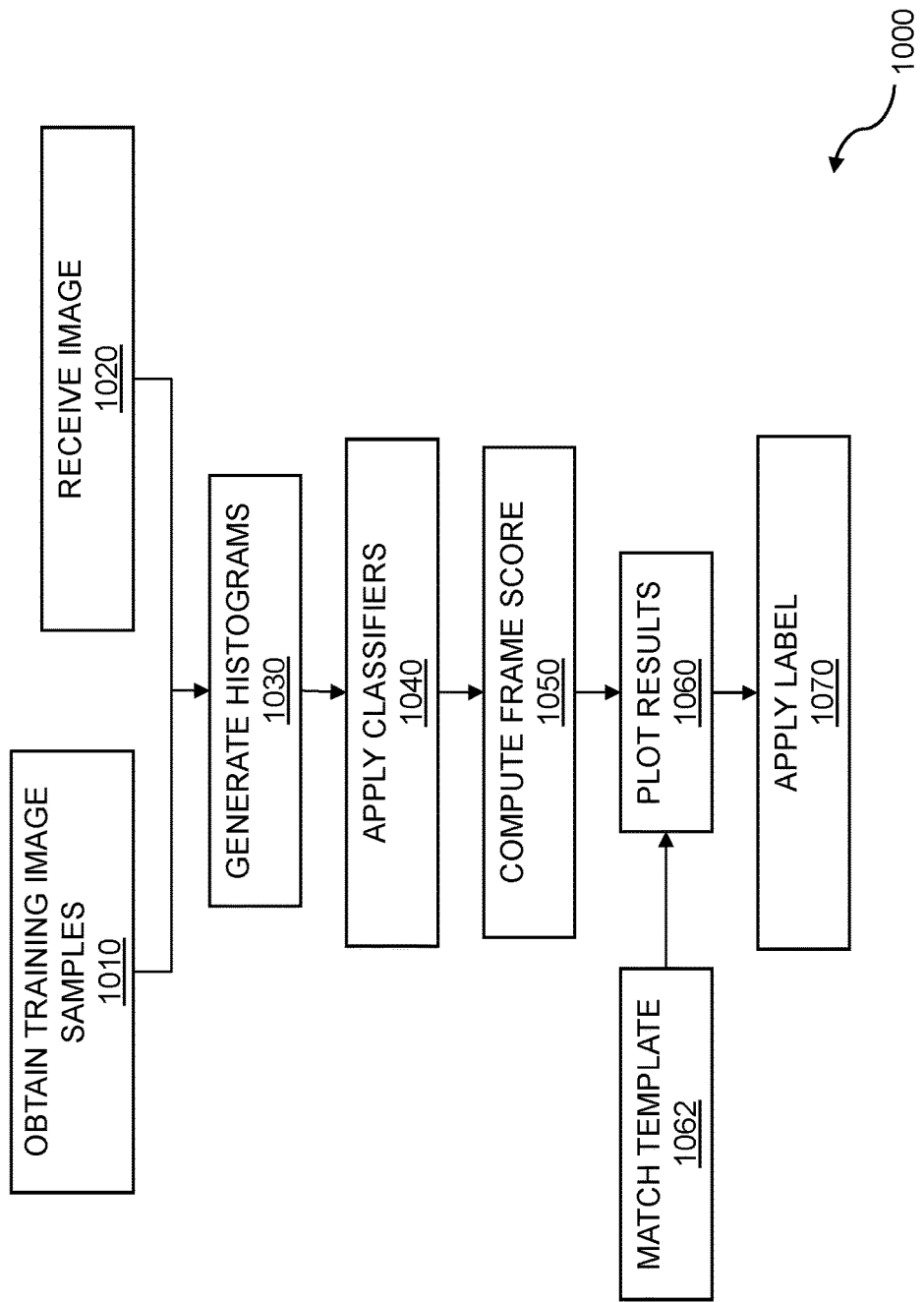
FIG. 10 is a flow diagram for detecting facial expressions.

FIG. 10 is a flow diagram for detecting facial expressions. Cognitive states can be determined by detecting and analyzing facial expressions in images. Vehicular cognitive data collection can use multiple devices. The collected vehicular cognitive data can include cognitive state data which is collected on an occupant of the vehicle from multiple sources. The multiple sources can include at least two sources of facial image data and can include audio data such as voice data. Analysis of the cognitive data is generated, and an output is rendered. The flow 1000, or portions thereof, can be implemented in semiconductor logic, accomplished using a mobile device, accomplished using a server device, and so on. The flow 1000 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1000 begins by obtaining training image samples 1010. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1000 continues with receiving an image 1020. The image can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1000 continues with generating histograms 1030 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1000 continues with applying classifiers 1040 to the histograms. The classifiers can be used to estimate probabilities, where the probabilities can correlate with an intensity of an AU or an expression. In some embodiments, the choice of classifiers used is based on the training of a supervised learning technique to identify facial expressions.

The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1000 continues with computing a frame score 1050. The score computed for an image, where the image can be a frame from a video, can be used to determine the presence of a facial expression in the image or video frame. The score can be based on one or more versions of the image 1020 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1000 continues with plotting results 1060. The results that are plotted can include one or more scores for one or more frames computed over a given time t. For example, the plotted results can include classifier probability results from analysis of HoGs for a sequence of images and video frames. The plotted results can be matched with a template 1062. The template can be temporal and can be represented by a centered box function or another function. A best fit with one or more templates can be found by computing a minimum error. Other best-fit techniques can include polynomial curve fitting, geometric curve fitting, and so on. The flow 1000 continues with applying a label 1070. The label can be used to indicate that a particular facial expression has been detected in the one or more images or video frames which constitute the image 1020 that was received. The label can be used to indicate that any of a range of facial expressions has been detected, including a smile, an asymmetric smile, a frown, and so on. Various steps in the flow 1000 may be changed in order, repeated, omitted, or the like without departing from the disclosed concepts. Various embodiments of the flow 1000 can be included in a computer program product embodied in a non-transitory computer readable medium that includes code executable by one or more processors. Various embodiments of the flow 1000, or portions thereof, can be included on a semiconductor chip and implemented in special purpose logic, programmable logic, and so on.

Figure 11:
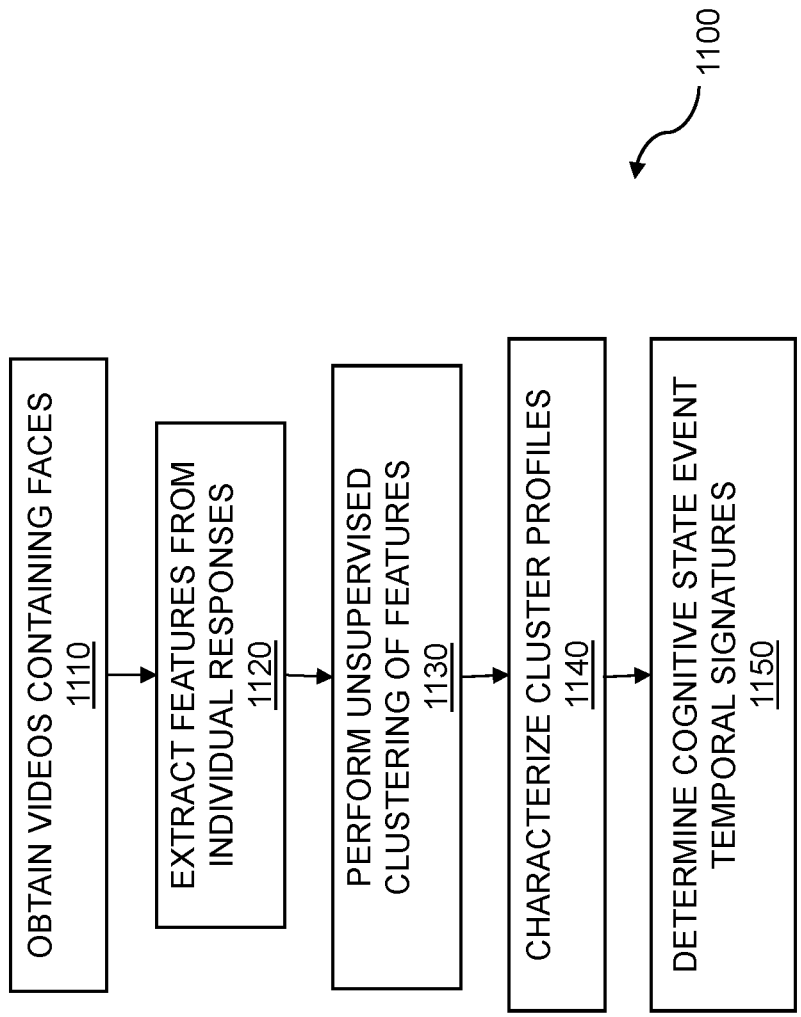
FIG. 11 is a flow diagram for the large-scale clustering of facial events.

FIG. 11 is a flow diagram for the large-scale clustering of facial events. Vehicular cognitive data collection uses multiple devices. Cognitive state data is obtained on an occupant of the vehicle. The cognitive state data includes at least two sources of facial image data and can include audio data such as voice data. Analysis of the cognitive state data is generated, and an output is rendered based on the analysis. The cognitive state data is tagged, where the data is tagged with an identity value for the occupant of the vehicle. Cognitive state events can include facial events, speech events, etc. The large-scale clustering of facial events can be performed for data collected from a remote computing device. The facial events can be collected from people as they interact with a vehicle. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1100 includes obtaining videos containing faces 1110. The videos can be obtained using one or more cameras, where the cameras can include a webcam coupled to one or more devices employed by the one or more people using the web-based framework. The flow 1100 continues with extracting features from the individual responses 1120. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1100 continues with performing unsupervised clustering of features 1130. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1100 includes characterizing cluster profiles 1140. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared across various demographic groups, where the groups can be formed based on geographic location, age, ethnicity, gender, and so on.

The flow 1100 can include determining cognitive state event temporal signatures 1150. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify or infer one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1100 may be changed in order, repeated, omitted, or the like without departing from the disclosed concepts. Various embodiments of the flow 1100 can be included in a computer program product embodied in a non-transitory computer readable medium that includes code executable by one or more processors. Various embodiments of the flow 1100, or portions thereof, can be included on a semiconductor chip and implemented in special purpose logic, programmable logic, and so on.

Figure 12:
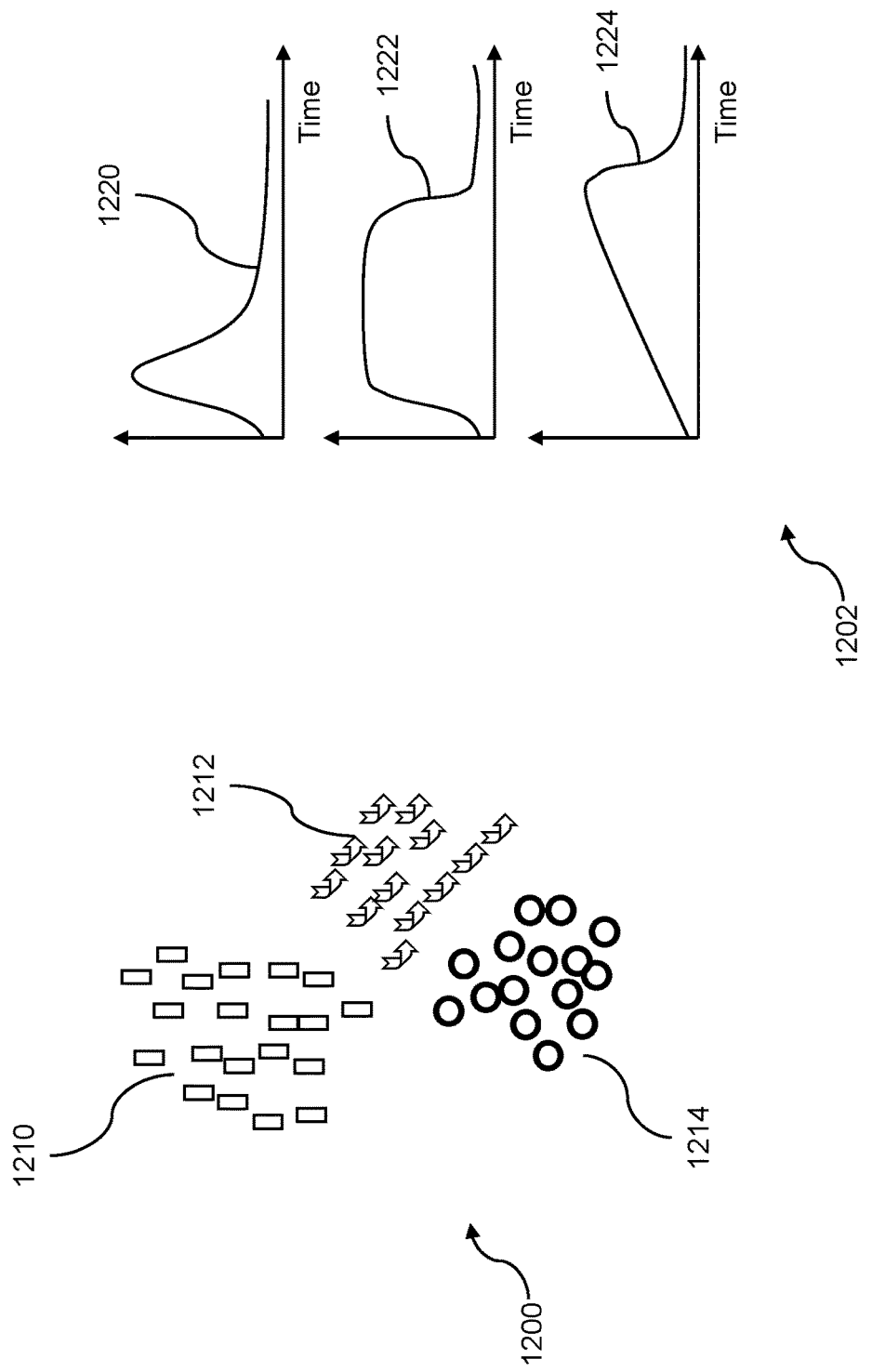
FIG. 12 shows unsupervised clustering of features and characterizations of cluster profiles.

FIG. 12 shows unsupervised clustering of features and characterizations of cluster profiles. Vehicular cognitive data collection uses multiple devices to support cognitive state analysis. Cognitive state data is obtained which is collected on an occupant of the vehicle from multiple sources, where the multiple sources include at least two sources of facial image data. Analysis of the cognitive state data is generated, and an output is rendered based on the analysis. The clustering of features and characterizations of cluster profiles can be performed for data collected from a remote computing device. The clustering of features and characterizations of cluster profiles can be performed for people as they interact with a vehicle. The sub-sectional components can be used with performing the evaluation of content of the face. The sub-sectional components can be used to provide a context. Features including samples of facial data can be clustered using unsupervised clustering. Various clusters can be formed which include similar groupings of facial data observations. The example 1200 shows three clusters, clusters 1210, 1212, and 1214. The clusters can be based on video collected from people who have opted-in to video collection. When the data collected is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1202 can be generated based on the clusters that can be formed from unsupervised clustering, with time shown on the x-axis and intensity or frequency shown on the y-axis. The cluster profiles can be based on captured facial data, including facial expressions. The cluster profile 1220 can be based on the cluster 1210, the cluster profile 1222 can be based on the cluster 1212, and the cluster profile 1224 can be based on the cluster 1214. The cluster profiles 1220, 1222, and 1224 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 13A:
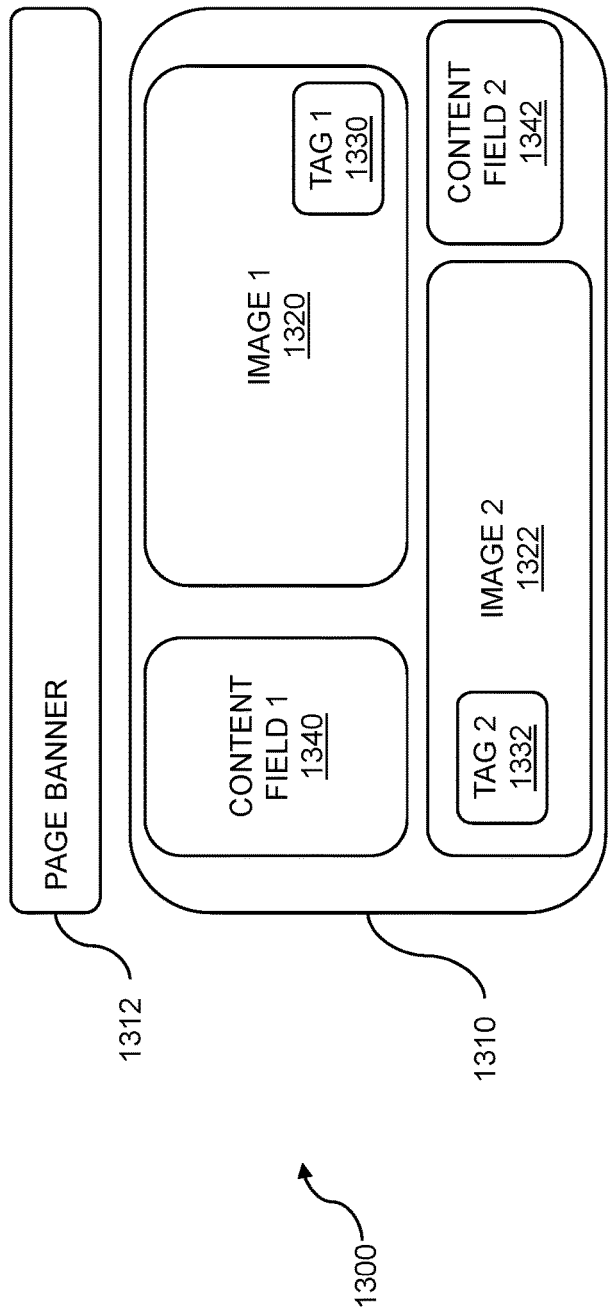
FIG. 13A shows example tags embedded in a webpage.

FIG. 13A shows example tags embedded in a webpage. Vehicle cognitive data collection uses multiple devices. The vehicular cognitive data collection can support cognitive state analysis. In some embodiments, screens within a vehicle can use embedded tags. Cognitive state data is obtained which is collected on an occupant of the vehicle from multiple sources. The multiple sources include at least two sources of facial image data and can include audio data. Analysis is generated of the cognitive state data which is collected from the multiple sources, and an output is rendered. The tags embedded in the webpage can be used for image analysis for data collected from a remote computing device. The tags embedded in the webpage can be used by people as they interact with a vehicle. Once a tag is detected, a mobile device, a server, semiconductor-based logic, etc. can be used to evaluate associated facial expressions. A webpage 1300 can include a page body 1310, a page banner 1312, and so on. The page body can include one or more objects, where the objects can include text, images, videos, audio, and so on. The example page body 1310 shown includes a first image, image 1 1320; a second image, image 2 1322; a first content field, content field 1 1340; and a second content field, content field 2 1342. In practice, the page body 1310 can contain multiple images and content fields and can include one or more videos, one or more audio presentations, and so on. The page body can include embedded tags, such as tag 1 1330 and tag 2 1332. In the example shown, tag 1 1330 is embedded in image 1 1320, and tag 2 1332 is embedded in image 2 1322. In embodiments, multiple tags are embedded. Tags can also be embedded in content fields, in videos, in audio presentations, etc. When a user mouses over a tag or clicks on an object associated with a tag, the tag can be invoked. For example, when the user mouses over tag 1 1330, tag 1 1330 can then be invoked. Invoking tag 1 1330 can include enabling a camera coupled to a user's device and capturing one or more images of the user as the user views a media presentation (or digital experience). In a similar manner, when the user mouses over tag 2 1332, tag 2 1332 can be invoked. Invoking tag 2 1332 can also include enabling the camera and capturing images of the user. In other embodiments, other actions are taken based on invocation of the one or more tags. Invoking an embedded tag can initiate an analysis technique, post to social media, award the user a coupon or another prize, initiate cognitive state analysis, perform emotion analysis, and so on.

Figure 13B:
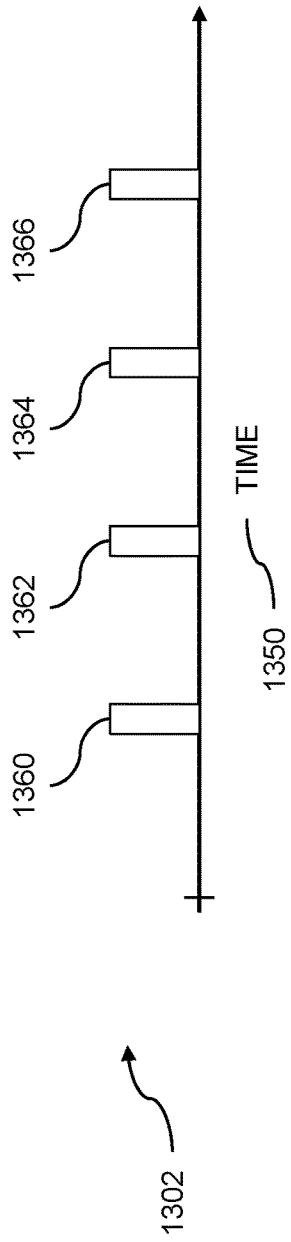
FIG. 13B shows invoking tags to collect images.

FIG. 13B shows invoking tags to collect images. Vehicular cognitive data collection uses multiple devices. Cognitive state data is obtained, from at least two sources, on an occupant of a vehicle. The cognitive state data can include facial image data, audio data, and so on. Analysis is generated of the cognitive state data. An output based on the analysis is rendered. The invoking tags to collect images can be used for image analysis of data collected from a remote computing device. The invoking tags to collect images can be used for people as they interact with a vehicle. As previously stated, a media presentation can be a video, a webpage, and so on. A video 1302 can include one or more embedded tags, such as a tag 1360, a second tag 1362, a third tag 1364, a fourth tag 1366, and so on. In practice, multiple tags can be included in the media presentation. The one or more tags can be invoked during the media presentation. The collection of the invoked tags can occur over time, as represented by a timeline 1350. When a tag is encountered in the media presentation, the tag can be invoked. When the tag 1360 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has indicated an opt-out, then invoking the tag 1360 neither enables the camera nor captures images of the user during the media presentation. The user can indicate an opt-in for certain types of participation, where opting-in can be dependent on specific content in the media presentation. For example, the user could opt-in to participation in a study of political campaign messages and not opt-in for a particular advertisement study. In this case, tags that are related to political campaign messages, advertising messages, social media sharing, etc. and that enable the camera and image capture when invoked would be embedded in the media presentation social media sharing, and so on. However, tags embedded in the media presentation that are related to advertisements would not enable the camera when invoked. Various other situations of tag invocation are also possible.

Figure 14:
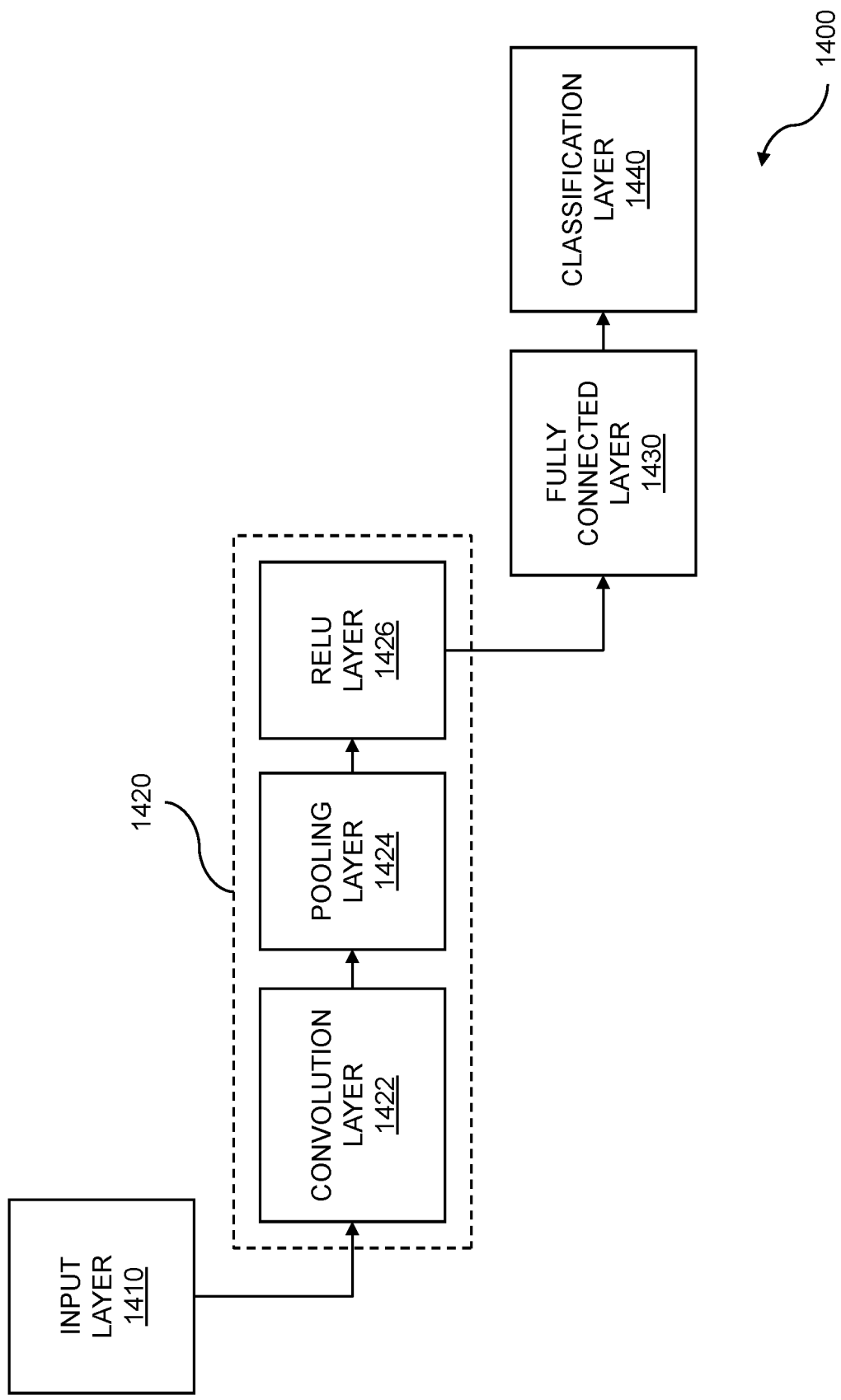
FIG. 14 is an example showing a convolutional neural network (CNN).

FIG. 14 is an example showing a convolutional neural network (CNN). The convolutional neural network can be used for deep learning, where the deep learning can be applied to vehicular cognitive data collection using multiple devices. Cognitive state data, such as facial data, audio data, etc., is obtained on an occupant of a vehicle. Analysis of the cognitive state data is generated, and an output is rendered based on the analysis. The cognitive state data is collected from multiple sources and is tagged. The cognitive state data is tagged with an identity value for the occupant. The convolutional neural network can be applied to such tasks as cognitive state analysis, mental state analysis, mood analysis, emotional state analysis, and so on. Cognitive state data can include mental processes, where the mental processes can include attention, creativity, memory, perception, problem solving, thinking, use of language, or the like.

Cognitive analysis is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, and emotional states from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content.

The voice data analysis can be used to determine one or more cognitive states, moods, mental states, emotional states, etc.

The artificial neural network, such as a convolutional neural network, which forms the basis for deep learning is based on layers. The layers can include an input layer, a convolution layer, a fully connected layer, a classification layer, and so on. The input layer can receive input data such as image data, where the image data can include a variety of formats including pixel formats. The input layer can then perform processing such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 14 is an example showing a convolutional neural network 1400. The convolutional neural network can be used for deep learning, where the deep learning can be applied to avatar image animation using translation vectors. The deep learning system can be accomplished using a convolution neural network or other techniques. The deep learning can accomplish facial recognition and analysis tasks. The network includes an input layer 1410. The input layer 1410 receives image data. The image data can be input in a variety of formats, such as JPEG, TIFF, BMP, and GIF. Compressed image formats can be decompressed into arrays of pixels, wherein each pixel can include an RGB tuple. The input layer 1410 can then perform processing such as identifying boundaries of the face, identifying landmarks of the face, extracting features of the face, and/or rotating a face within the plurality of images.

The network includes a collection of intermediate layers 1420. The multilayered analysis engine can include a convolutional neural network. Thus, the intermediate layers can include a convolution layer 1422. The convolution layer 1422 can include multiple sublayers, including hidden layers within it. The output of the convolution layer 1422 feeds into a pooling layer 1424. The pooling layer 1424 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 1424. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 1426. The output of the pooling layer 1424 can be input to the RELU layer 1426. In embodiments, the RELU layer implements an activation function such as $f(x)-\max(0,x)$, thus providing an activation with a threshold at zero. In some embodiments, the RELU layer 1426 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1422 and one or more hidden layers, and wherein the multilayered analysis engine can be used for emotional analysis.

The example 1400 includes a fully connected layer 1430. The fully connected layer 1430 processes each pixel/data point from the output of the collection of intermediate layers 1420. The fully connected layer 1430 takes all neurons in the previous layer and connects them to every single neuron it has. The output of the fully connected layer 1430 provides input to a classification layer 1440. The output of the classification layer 1440 provides a facial expression and/or cognitive state as its output. Thus, a multilayered analysis engine such as the one depicted in FIG. 14 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt, or learn, as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include a person being more engaged, where engagement is based on affect, the person spending more time playing an online game or navigating a webpage, the person converting by buying a product or service, and so on. The reinforced learning can be based on exploring a solution space and adapting the model, algorithm, etc., based on outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 15:
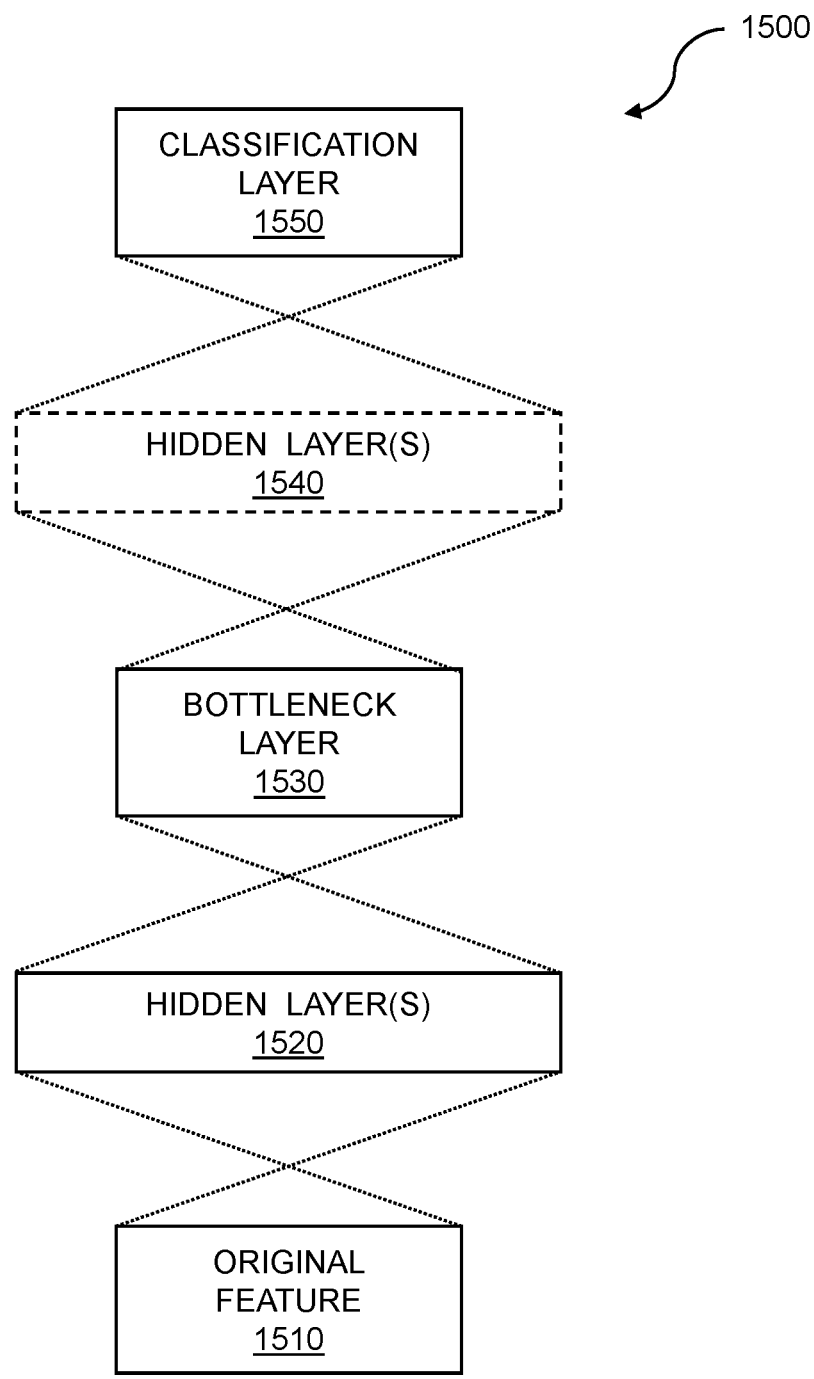
FIG. 15 illustrates a bottleneck layer within a deep learning environment.

FIG. 15 illustrates a bottleneck layer within a deep learning environment. A bottleneck layer can be one of a plurality of layers in a deep neural network. The bottleneck layer can be used for cognitive state analysis based on collected vehicular cognitive data. The vehicular cognitive data, which can include cognitive state data such as video data, audio data, and so on, can be collected using multiple devices. A deep neural network can apply classifiers such as image classifiers, audio classifiers, etc., weighs, and so on. The classifiers can be learned by analyzing cognitive state data. Cognitive state data is obtained on an occupant of a vehicle, and analysis of the cognitive state data is generated. An output is rendered based on the analysis.

Layers of a deep neural network can include a bottleneck layer 1500. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1510. A feature such as an image feature can include points, edges, objects, boundaries between and among regions, properties, and so on. The deep neural network can include one or more hidden layers 1520. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, individual bottleneck layers can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1530. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 1540. The number of the hidden layers can include zero hidden layers, one hidden layer, a plurality of hidden layers, and so on. The hidden layers following the bottleneck layer can include more nodes than the bottleneck layer. The deep neural network can include a classification layer 1550. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 16:
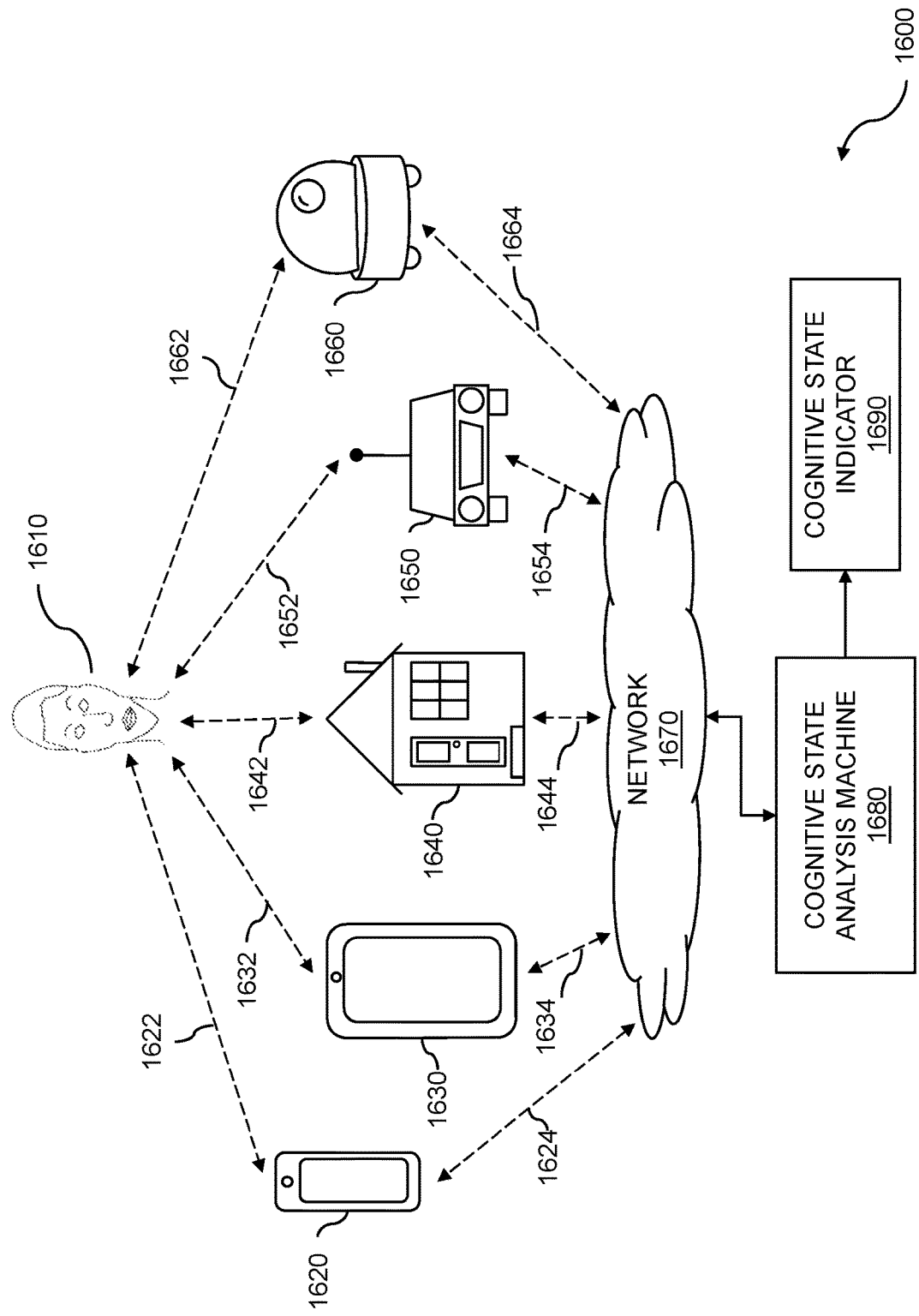
FIG. 16 shows data collection including devices and locations.

FIG. 16 shows data collection including devices and locations 1600. Vehicular cognitive data collection, where the cognitive data comprises cognitive state data including video data and audio data, uses multiple devices. A first computing device within a vehicle obtains cognitive state data which is collected from multiple sources on an occupant of the vehicle. A second computing device generates analysis of the cognitive state data. A third computing device renders an output based on the analysis of the cognitive state data. The multiple mobile devices, vehicles, and locations, can be used separately or in combination to collect video data on a user 1610. While one person is shown, the video data can be collected on multiple people. A user 1610 can be observed as she or he is performing a task, experiencing an event, viewing a media presentation, and so on. The user 1610 can be shown one or more media presentations, political presentations, social media, or another form of displayed media. The one or more media presentations can be shown to a plurality of people. The media presentations can be displayed on an electronic display coupled to a client device. The data collected on the user 1610 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1610 can be analyzed and viewed for a variety of purposes including expression analysis, mental state analysis, cognitive state analysis, and so on. The electronic display can be on a smartphone 1620 as shown, a tablet computer 1630, a personal digital assistant, a television, a mobile monitor, or any other type of electronic device. In one embodiment, expression data is collected on a mobile device such as a cell phone 1620, a tablet computer 1630, a laptop computer, or a watch. Thus, the multiple sources can include at least one mobile device, such as a phone 1620 or a tablet 1630, or a wearable device such as a watch or glasses (not shown). A mobile device can include a front-facing camera and/or a back-side camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1610, data can be collected in a house 1640 using a web camera or the like; in a vehicle 1650 using a web camera, client device, etc.; by a social robot 1660, and so on.

As the user 1610 is monitored, the user 1610 might move due to the nature of the task, boredom, discomfort, distractions, or for another reason. As the user moves, the camera with a view of the user's face can be changed. Thus, as an example, if the user 1610 is looking in a first direction, the line of sight 1622 from the smartphone 1620 is able to observe the user's face, but if the user is looking in a second direction, the line of sight 1632 from the tablet 1630 is able to observe the user's face. Furthermore, in other embodiments, if the user is looking in a third direction, the line of sight 1642 from a camera in the house 1640 is able to observe the user's face, and if the user is looking in a fourth direction, the line of sight 1652 from the camera in the vehicle 1650 is able to observe the user's face. If the user is looking in a fifth direction, the line of sight 1662 from the social robot 1660 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1610 can also use a wearable device including a camera for gathering contextual information and/or collecting expression data on other users. Because the user 1610 can move her or his head, the facial data can be collected intermittently when she or he is looking in a direction of a camera. In some cases, multiple people can be included in the view from one or more cameras, and some embodiments include filtering out faces of one or more other people to determine whether the user 1610 is looking toward a camera. All or some of the expression data can be continuously or sporadically available from the various devices and other devices.

The captured video data can include cognitive content, such as facial expressions, etc., and can be transferred over a network 1670. The network can include the Internet or other computer network. The smartphone 1620 can share video using a link 1624, the tablet 1630 using a link 1634, the house 1640 using a link 1644, the vehicle 1650 using a link 1654, and the social robot 1660 using a link 1664. The links 1624, 1634, 1644, 1654, and 1664 can be wired, wireless, and hybrid links. The captured video data, including facial expressions, can be analyzed on a cognitive state analysis machine 1680, on a computing device such as the video capture device, or on another separate device. The cognitive state analysis machine can include a cognitive state analysis engine. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 1690. The cognitive state indicator 1690 can indicate cognitive states, mental states, moods, emotions, etc. In embodiments, the cognitive states that can be inferred include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 17:
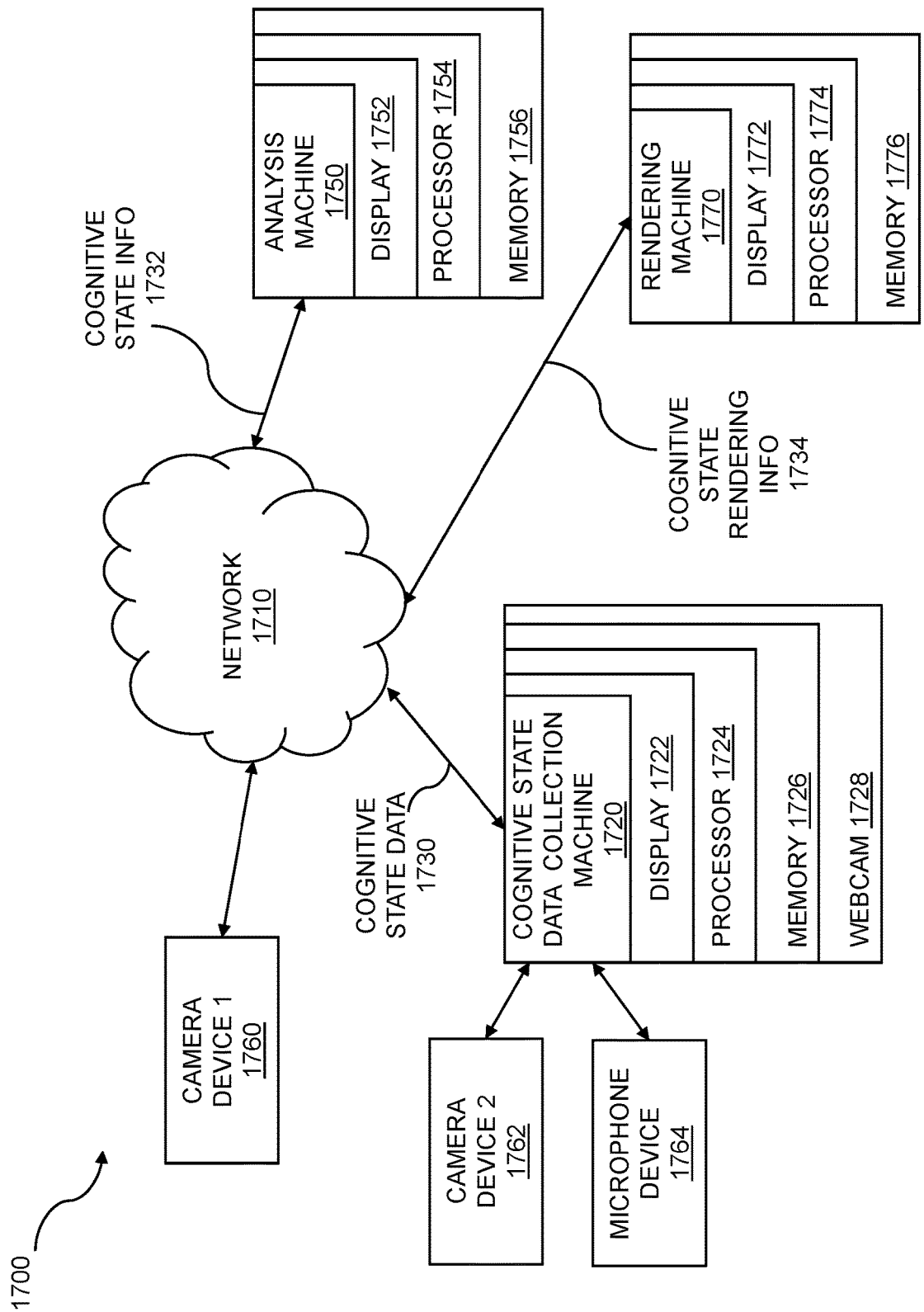
FIG. 17 is a system diagram for cognitive state analysis.

FIG. 17 is a system diagram for cognitive state analysis. The system 1700 can include one or more processors coupled together by a communication link such as network 1710. The network can include the Internet, a local area network (LAN), a wide area network (WAN), a wireless network, and so on. The system 1700 can also include two or more cameras that can be linked to the one or more machines and/or directly to a communication link. The system 1700 can include a cognitive state data collection machine 1720, which, in some embodiments, is also referred to as a client machine. The cognitive state data collection machine 1720 includes a memory 1726 which stores instructions, data, and the like, one or more processors 1724 coupled to the memory, a display 1722, and a webcam 1728. The display 1722 may be any electronic display, including but not limited to, a computer display, a laptop screen, a net-book screen, a tablet screen, a smartphone display, a personal digital assistant (PDA) display, a mobile device display, a remote with a display, a television, a projector, or the like. The webcam 1728, as the term is used herein, may refer to a camera on a computer (such as a laptop, a net-book, a desktop, a tablet, or the like), a video camera, a still camera, a cell phone camera, a mobile device camera (including, but not limited to, a front-side camera), a thermal imager, a CCD device, a three-dimensional camera, a depth camera, a light field camera, and multiple webcams used to capture different views of viewers or any other type of image capture apparatus that may allow image data captured to be used by an electronic system.

An individual can interact with the cognitive state data collection machine 1720, interact with another machine, or view a media presentation on another electronic display, among other activities. The system 1700 can include a computer program product embodied in a non-transitory computer readable medium for cognitive state analysis, the computer program product comprising code which causes one or more processors to perform operations of obtaining cognitive state data which is collected on an occupant of a vehicle from multiple sources, wherein the multiple sources include at least two sources of facial image data; generating analysis of the cognitive state data which is collected from the multiple sources; and rendering an output based on the analysis of the cognitive state data. Thus, the system 1700 can enable a computer-implemented method for cognitive state analysis including: obtaining, on a first computing device within a vehicle, cognitive state data which is collected on an occupant of the vehicle from multiple sources, wherein the multiple sources include at least two sources of facial image data; generating, using a second computing device, analysis of the cognitive state data which is collected from the multiple sources; and rendering, on a third computing device, an output based on the analysis of the cognitive state data. The multiple sources can include two or more of the webcam 1728, a first camera device 1760 linked through the network 1710, and/or a second camera device 1762 linked directly to the cognitive state data collection machine 1720, and/or a microphone device 1764 which can be linked directly to the cognitive state data collection machine or can be linked via the network 1710. In some embodiments, the cognitive state data collection machine 1720 can send cognitive state data 1730 to another machine, such as the analysis machine 1750.

Some embodiments can include a web service or analysis machine 1750. The analysis machine 1750 includes one or more processors 1754 coupled to a memory 1756 to store instructions. Some embodiments of the analysis machine 1750 include a display 1752. The one or more processors 1754 can be configured to receive cognitive state data from the cognitive state data collection machine 1720, the first camera device 1760, and/or other machines configured to collect cognitive state data; the cognitive state data can include data from at least two sources that can be coupled to one or more machines. The one or more processors 1754 can then analyze the cognitive state data received and provide cognitive state information 1732. The analysis can produce cognitive state information, inferred cognitive states, emotigraphs, actigraphs, other textual/graphical representations, or any other type of analysis. In some embodiments, analysis of the cognitive state data is augmented by a human coder. The analysis machine 1750 can display at least some of the analysis on the display 1752 and/or can provide the analysis of the cognitive state data to a client machine such as the cognitive state data collection machine 1720 or another client machine, such as the rendering machine 1770, to be displayed to a user. The data sent to the rendering machine 1770 can include cognitive state rendering information 1734 sent via network 1710. So, the system 1700 can enable a method for receiving cognitive state data which is collected on an individual from multiple sources, wherein the multiple sources include at least two sources of facial data and/or audio data, analyzing the cognitive state data which is collected from multiple sources, and providing the analysis of the cognitive state data to a rendering, or client, machine 1770. In some embodiments, the analysis machine 1750 can be provisioned as a web server with the analysis of the cognitive state data obtained from a web service.

Some embodiments include a rendering, or second client, machine 1770. The rendering machine 1770 includes one or more processors 1774 coupled to memory 1776 to store instructions, and a display 1772. The client machine can receive the analysis of the cognitive state data from the analysis machine, or server 1750, and can render an output to the display 1772. The system 1700 can enable a computer-implemented method for cognitive state analysis comprising receiving analysis of cognitive state data which is collected on an individual from multiple sources wherein the multiple sources include at least two sources of facial data and rendering an output based on the analysis of the cognitive state data.

Embodiments include a computer system for cognitive state analysis comprising: a memory which stores instructions; one or more processors coupled to the memory wherein the one or more processors, when executing the instructions which are stored, are configured to: obtain, on a first computing device within a vehicle, cognitive state data which is collected on an occupant of the vehicle from multiple sources, wherein the multiple sources include at least two sources of facial image data, and wherein at least one face is partially occluded; generate, using a second computing device, analysis of the cognitive state data which is collected from the multiple sources; and render, on a third computing device, an output based on the analysis of the cognitive state data.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more substeps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are limited to neither conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A computer-implemented method for cognitive state analysis comprising:
   obtaining, on a first computing device within a vehicle, cognitive state data which is collected on an occupant of the vehicle, wherein the face of the occupant is partially occluded;
   inferring estimated cognitive state data for the occupant, wherein the cognitive state data collected is intermittent, wherein the inferring generates estimated data for time periods during which cognitive state data was not collected;
   generating, using a second computing device, an analysis of the cognitive state data which is collected from the occupant of the vehicle;
   determining a perception metric, based on the cognitive state data, for the occupant of the vehicle; and
   rendering an output, for the occupant in the vehicle, based on the analysis of the cognitive state data and the perception metric.

2. The method of claim 1 wherein the perception metric includes a cognitive load for the occupant.

3. The method of claim 1 wherein the perception metric includes an activity by the occupant.

4. The method of claim 1 wherein the perception metric includes an involvement metric by the occupant.

5. The method of claim 1 wherein the perception metric includes a distractedness, drowsiness, or impairment evaluation for the occupant.

6. The method of claim 1 wherein the cognitive state data is obtained from multiple sources.

7. The method of claim 6 wherein the multiple sources include at least two sources of facial image data.

8. The method of claim 6 wherein the analysis includes aggregating the cognitive state data from the multiple sources.

9. The method of claim 1 wherein the partial occluding comprises a time basis of occluding.

10. The method of claim 1 wherein the partial occluding comprises an image basis of occluding.

11. The method of claim 1 wherein the cognitive state data is tagged.

12. The method of claim 11 wherein the cognitive state data is tagged with an identity value for the occupant of the vehicle.

13. The method of claim 11 wherein the cognitive state data is tagged with information on a context in which the cognitive state data was collected.

14. The method of claim 11 further comprising partitioning the cognitive state data based on tagging.

15. The method of claim 1 further comprising collecting audio data and augmenting the cognitive state data with the audio data.

16. The method of claim 15 wherein the audio data enables analyzing cognitive state data for the face that is partially occluded.

17. The method of claim 1 wherein the cognitive state data comprises facial image data that is collected intermittently while the occupant's face is partially occluded.

18. The method of claim 1 further comprising interpolating cognitive state data when the cognitive state data collected is intermittent.

19. The method of claim 1 further comprising imputing additional cognitive state data for one or more time periods during which no cognitive state data was collected.

20. The method of claim 1 further comprising determining contextual information.

21. The method of claim 1 wherein the rendering is used to provide vehicle performance data to one or more occupants of the vehicle.

22. The method of claim 1 wherein the rendering is used to provide vehicle control to one or more occupants of the vehicle.

23. The method of claim 1 further comprising:
displaying the rendering in visual format to one or more occupants of the vehicle;
delivering an auditory message complementing the rendering, wherein the auditory message provides clarification of the rendering;
soliciting, using a digital voice, verbal feedback from a primary occupant of the vehicle; and
controlling operation of the vehicle, based on the verbal feedback that was solicited and the analysis of the cognitive state data.

24. A computer program product embodied in a non-transitory computer readable medium for cognitive state analysis, the computer program product comprising code which causes one or more processors to perform operations of:
obtaining, on a first computing device within a vehicle, cognitive state data which is collected on an occupant of the vehicle, wherein the face of the occupant is partially occluded;
inferring estimated cognitive state data for the occupant, wherein the cognitive state data collected is intermittent, wherein the inferring generates estimated data for time periods during which cognitive state data was not collected;
generating, using a second computing device, an analysis of the cognitive state data which is collected from the occupant of the vehicle;
determining a perception metric, based on the cognitive state data, for the occupant of the vehicle; and
rendering an output, for the occupant in the vehicle, based on the analysis of the cognitive state data and the perception metric.

25. A computer system for cognitive state analysis comprising:
a memory which stores instructions;
one or more processors coupled to the memory wherein the one or more processors, when executing the instructions which are stored, are configured to:
obtain, on a first computing device within a vehicle, cognitive state data which is collected on an occupant of the vehicle, wherein the face of the occupant is partially occluded;
infer estimated cognitive state data for the occupant, wherein the cognitive state data collected is intermittent, wherein the inferring generates estimated data for time periods during which cognitive state data was not collected;
generate, using a second computing device, an analysis of the cognitive state data which is collected from the occupant of the vehicle;
determine a perception metric, based on the cognitive state data, for the occupant of the vehicle; and
render an output, for the occupant in the vehicle, based on the analysis of the cognitive state data and the perception metric.

26. The method of claim 14 further comprising partitioning video data into video segments, wherein the partitioning is based on facial events within the cognitive state data.

* * * * *